United States Patent
Karanam et al.

(10) Patent No.: US 11,282,218 B2
(45) Date of Patent: Mar. 22, 2022

(54) SYSTEMS AND METHODS FOR PROVIDING MEDICAL GUIDANCE USING A PATIENT DEPTH IMAGE

(71) Applicant: SHANGHAI UNITED IMAGING INTELLIGENCE CO., LTD., Shanghai (CN)

(72) Inventors: Srikrishna Karanam, Brighton, MA (US); Ziyan Wu, Lexington, MA (US)

(73) Assignee: Shanghai United Imaging Intelligence Co., Ltd., Shanghai (CN)

( * ) Notice: Subject to any disclaimer, the term of this patent is extended or adjusted under 35 U.S.C. 154(b) by 136 days.

(21) Appl. No.: 16/694,456

(22) Filed: Nov. 25, 2019

(65) Prior Publication Data
US 2021/0158550 A1    May 27, 2021

(51) Int. Cl.
*G06T 7/50* (2017.01)
*G06T 7/73* (2017.01)
*G16H 30/20* (2018.01)
*G06N 20/00* (2019.01)
*G06T 7/00* (2017.01)
*G06T 17/00* (2006.01)

(52) U.S. Cl.
CPC ............... *G06T 7/50* (2017.01); *G06N 20/00* (2019.01); *G06T 7/0014* (2013.01); *G06T 7/74* (2017.01); *G06T 7/75* (2017.01); *G06T 17/00* (2013.01); *G16H 30/20* (2018.01); *G06T 2207/10028* (2013.01); *G06T 2207/20081* (2013.01); *G06T 2207/30196* (2013.01); *G06T 2210/41* (2013.01)

(58) Field of Classification Search
CPC .... G06T 7/50; G06T 7/74; G06T 7/75; G06T 7/0014; G06T 17/00; G06T 2207/10028; G06T 2207/20081; G06T 2207/30196; G06T 2210/41; G16H 30/20; G06N 20/00
See application file for complete search history.

(56) References Cited

U.S. PATENT DOCUMENTS

| | | | |
|---|---|---|---|
| 10,621,779 B1 * | 4/2020 | Topiwala | G06T 7/62 |
| 2019/0278983 A1 * | 9/2019 | Iqbal | G06K 9/00355 |
| 2019/0332900 A1 * | 10/2019 | Sjolund | G16H 30/40 |
| 2020/0167650 A1 * | 5/2020 | Lamy-Poirier | G06N 3/0454 |
| 2020/0258243 A1 * | 8/2020 | Chang | A61B 5/7267 |

* cited by examiner

*Primary Examiner* — Xin Sheng
(74) *Attorney, Agent, or Firm* — Faegre Drinker Biddle & Reath LLP

(57) ABSTRACT

Methods and systems for using a patient representation model including a feature extraction model and a parameter determining model. For example, a computer-implemented method includes receiving, by a first feature extraction model, a depth image; generating, by the first feature extraction model, a first feature vector corresponding to the depth image; determining, by a parameter determining model, a plurality of three-dimensional model parameters based at least in part on the first feature vector; receiving a ground truth; determining a deviation between the ground truth and information associated with the plurality of three-dimensional model parameters; changing, based at least in part on the deviation, one or more parameters of the patient representation model; receiving a first patient image; determining a plurality of three-dimensional patient parameters based at least in part on the first patient image; and providing the plurality of three-dimensional patient parameters as medical guidance.

20 Claims, 8 Drawing Sheets

SYSTEMS AND METHODS FOR PROVIDING MEDICAL GUIDANCE USING A PATIENT DEPTH IMAGE

1. BACKGROUND OF THE INVENTION

Certain embodiments of the present invention are directed to medical guidance. More particularly, some embodiments of the invention provide methods and systems for providing medical guidance using a patient depth image. Merely by way of example, some embodiments of the invention are configured to provide guidance for medical scanning. But it would be recognized that the invention has a much broader range of applicability.

Patient positioning and modeling are often a crucial step in many medical environments to help guide medical workers in making decisions, such as ones related to medical treatment plans, or parameter settings for a medical examination apparatus. The estimation of a human pose may involve estimating a parametric human mesh model given an input image that corresponds to a patient. Such input image is typically two-dimensional and may include two-dimensional key points of interest that may be used to find model parameters. Model parameters may also be estimated without such key points and instead directly from the two-dimensional input image, such as based on regression algorithms. Conventional estimation methods, however, suffer from several issues that limits estimation accuracy. For example, conventional estimation methods are ill-equipped to solve depth ambiguity programs where multiple three-dimensional configurations may explain the same two-dimensional image. In yet another example, conventional estimation methods lack constraints for limiting their estimation to be in accordance with realistic human shape and pose. It is therefore a need for systems and methods for providing medical guidance using a patient depth image that is designed to solve the depth ambiguity problem and to impose constraints to generate realistic estimates.

2. BRIEF SUMMARY OF THE INVENTION

Certain embodiments of the present invention are directed to medical guidance. More particularly, some embodiments of the invention provide methods and systems for providing medical guidance using a patient depth image. Merely by way of example, some embodiments of the invention are configured to provide guidance for medical scanning. But it would be recognized that the invention has a much broader range of applicability.

In various embodiments, a computer-implemented method for providing medical guidance using a patient representation model (e.g., a model including one or more feature extraction models and a parameter determining model) includes: receiving, by a first feature extraction model, a depth image; generating, by the first feature extraction model, a first feature vector corresponding to the depth image; determining, by a parameter determining model, a plurality of three-dimensional model parameters based at least in part on the first feature vector; receiving a ground truth; determining a deviation between the ground truth and information associated with the plurality of three-dimensional model parameters; changing, based at least in part on the deviation, one or more parameters of the patient representation model. In certain examples, such as after the changing one or more parameters of the patient representation model, the method further includes providing medical guidance by at least: receiving, by the first feature extraction model, a first patient image; determining, by the parameter determining model, a plurality of three-dimensional patient parameters based at least in part on the first patient image; and providing the plurality of three-dimensional patient parameters as medical guidance. In certain examples, the computer-implemented method is performed by one or more processors.

In various embodiments, a computer-implemented method for providing medical guidance includes: receiving, by a first feature extraction model, a depth image; receiving, by a second feature extraction model, a two-dimensional image; generating, by the first feature extraction model, a first feature vector corresponding to the depth image; generating, by the second feature extraction model, a second feature vector corresponding to the two-dimensional image; concatenating the first feature vector and the second feature vector into a concatenated feature vector; determining, by a parameter determining model, a plurality of three-dimensional patient parameters based at least in part on the concatenated feature vector; and providing the plurality of three-dimensional patient parameters as medical guidance. In certain examples, the computer-implemented method is performed by one or more processors.

In various embodiments, a system for providing medical guidance includes: an image receiving module configured to receive, by a first feature extraction model, a depth image, and receive, by a second feature extraction model, a two-dimensional image; a feature vector generating module configured to generate, by the first feature extraction model, a first feature vector corresponding to the depth image, and generate, by the second feature extraction model, a second feature vector corresponding to the two-dimensional image; a vector concatenating module configured to concatenate the first feature vector and the second feature vector into a concatenated feature vector; a parameter determining module configured to determine, by a parameter determining model, a plurality of three-dimensional patient parameters based at least in part on the concatenated feature vector; and a guidance providing module configured to provide the plurality of three-dimensional patient parameters as medical guidance.

Depending upon embodiment, one or more benefits may be achieved. These benefits and various additional objects, features and advantages of the present invention can be fully appreciated with reference to the detailed description and accompanying drawings that follow.

3. BRIEF DESCRIPTION OF THE DRAWINGS

4. DETAILED DESCRIPTION OF THE INVENTION

Certain embodiments of the present invention are directed to medical guidance. More particularly, some embodiments of the invention provide methods and systems for providing medical guidance using a patient depth image. Merely by way of example, some embodiments of the invention are configured to provide guidance for medical scanning. But it would be recognized that the invention has a much broader range of applicability.

Figure 1:
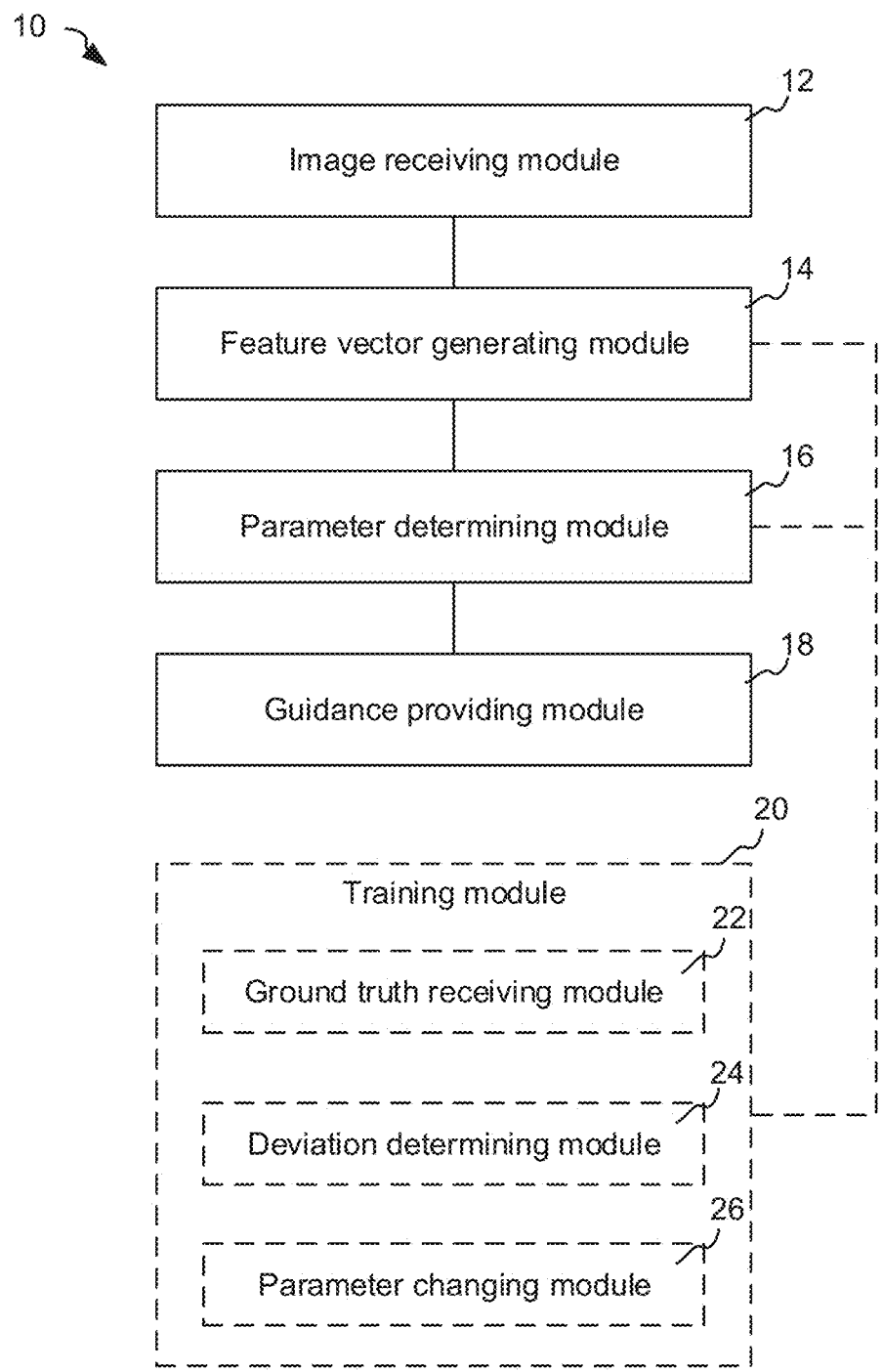
FIG. 1 is a simplified diagram showing a system for providing medical guidance, according to some embodiments.

FIG. 1 is a simplified diagram showing a system for providing medical guidance, according to some embodiments. This diagram is merely an example, which should not unduly limit the scope of the claims. One of ordinary skill in the art would recognize many variations, alternatives, and modifications. In some examples, the system 10 includes an image receiving module 12, a feature vector generating module 14, a parameter determining module 16, and a guidance providing module 18. In some examples, the system 10 is configured to use, control, and/or instruct a patient representation model for providing medical guidance. In certain examples, the patient representation model includes one or more feature extraction models, one or more parameter determining models, and/or one or more distribution generating models. For example, the patient representation model includes a first feature extraction model, a second feature extraction mode, a parameter determining model, and/or a distribution generating model. In various examples, the system is configured to reduce patient representation problems involving depth ambiguity. Although the above has been shown using a selected group of components, there can be many alternatives, modifications, and variations. For example, some of the components may be expanded and/or combined. Some components may be removed. Other components may be inserted to those noted above. Depending upon the embodiment, the arrangement of components may be interchanged with others replaced.

In various embodiments, the image receiving module 12 is configured to receive one or more images, such as by one or more feature extraction models. In some examples, the image receiving module 12 is configured to input one or more images into the one or more feature extraction models. In certain examples, the image receiving module 12 is configured to receive one or more training images by the one or more feature extraction models for training the patient representation model. In various examples, the image receiving module 12 is configured to receive one or more patient images. In some examples, the image receiving module 12 is configured to receive, by a first feature extraction model, a depth image. In some examples, the image receiving module 12 is configured to input the depth image into the first feature extraction model. In some examples, the image receiving module 12 is configured to receive, by a second feature extraction model, a two-dimensional image. In some examples, the image receiving module 12 is configured to input the two-dimensional image into the second feature extraction model. In certain examples, a patient image is a depth image or a two-dimensional image. In certain examples, a training image is a depth image or a two-dimensional image. In various examples, a training image is a previously analyzed patient image.

In various embodiments, the feature vector generating module 14 is configured to generate, such as by the one or more feature extraction models, one or more feature vectors corresponding to the one or more images received by the one or more feature extraction models. In certain examples, the feature vector generating module 14 is configured to generate, by the first feature extraction model, a first feature vector corresponding to the depth image. In certain examples, the feature vector generating module is configured to generate, by the second feature extraction model, a second feature vector corresponding to the two-dimensional image.

In various embodiments, the parameter determining module 16 is configured to determine, such as by the parameter determining model, a plurality of parameters based at least in part on one or more feature vectors. In certain examples, the plurality of parameters is a plurality of three-dimensional patient parameters that corresponds to a patient's body. In certain examples, the plurality of three-dimensional patient parameters includes a pose parameter and/or a shape parameter. In some examples, the parameter determining module 16 is configured to determine, by the parameter determining model, a plurality of three-dimensional patient parameters based at least in part on the first feature vector, the second feature vector, and/or a concatenated feature vector (e.g., one obtained by concatenating the first feature vector and the second feature vector. In various embodiments, the system 10 further includes a vector concatenating module 22 configured to concatenate the first feature vector and the second feature vector into a concatenated feature vector.

In various embodiments, the guidance providing module 18 is configured to provide medical guidance. In certain examples, the guidance providing module 18 is configured to provide the plurality of three-dimensional patient parameters as medical guidance. In some examples, the guidance providing module 18 is configured to generate a three-dimensional patient representation based at least in part on the plurality of three-dimensional patient parameters. In certain examples, the system 10 includes a separate representation module configured to generate the three-dimensional patient representation based at least in part on the plurality of three-dimensional patient parameters. In various examples, the guidance providing module 18 is configured to provide the three-dimensional patient representation as medical guidance. In some examples, the three-dimensional patient representation includes an image, a kinematic model, a skeleton model, a surface model, a mesh model, a fitted model, and/or a point cloud. In certain examples, the medical guidance includes guidance for medical scanner positioning, medical scanning parameters optimization; and/or medical treatment sequence planning. For example, the medical guidance provides pose, shape, and/or size information of the patient to help medical personnel to determine the appropriate scanning protocol, such as for an MR, X-Ray, or CT examination.

In various embodiments, the system 10 further includes a training module 20 configured to train the patient representation model. In certain examples, the system 10 is coupled to a separate training module 20 that is not part of system 10. In some examples, the training module 20 is configured to train the first feature extraction model, the second feature extraction model, and/or the parameter determining model. In some examples, the training module 20 includes a ground truth receiving module 22, a deviation determining module 24, and a parameter changing module 26.

In various embodiments, the ground truth receiving module 22 is configured to receive a ground truth. In various examples, the ground truth receiving module 22 is configured to receive a ground truth corresponding to the depth image and/or to the two-dimensional image. In some examples, the ground truth receiving module 22 is configured to receive a plurality of ground truth model parameters corresponding to the depth image and/or to the two-dimensional image. For example, the ground truth receiving module 22 is configured to receive the plurality of ground truth model parameters as the ground truth. In certain examples, the ground truth receiving module 22 is configured to receive a normal distribution (e.g., a Gaussian distribution with zero mean and unit variance). For example, the ground truth receiving module 22 is configured to receive the normal distribution as the ground truth. In various examples, the ground truth receiving module 22 is configured to receive one or more reference feature locations corresponding to the two-dimensional image. For example, the ground truth receiving module 22 is configured to receive the one or more reference feature locations as the ground truth. In some examples, the ground truth receiving module 22 is configured to receive one or more reference feature depths corresponding to the depth image. For example, the ground truth receiving module 22 is configured to receive the one or more reference feature depths as the ground truth.

In various embodiments, the deviation determining module 24 is configured to determine a deviation based at least in part on the ground truth and information associated with the plurality of three-dimensional model parameters. In some examples, the deviation determining module 24 is configured to determine a deviation between the ground truth and information associated with the plurality of three-dimensional model parameters. In certain examples, the deviation determining module 24 is configured to determine a deviation distance (e.g., Euclidean distance) between the plurality of three-dimensional model parameters and the plurality of ground truth model parameters.

In some embodiments, the system 10 and/or the training module 20 further includes a feature depth determining module configured to determine one or more target feature depths corresponding to the depth image based at least in part on the three-dimensional model parameters. In various examples, the deviation determining module 24 is configured to determine one or more depth deviations between the one or more target feature depths and the one or more reference feature depths. In some embodiments, the system 10 and/or the training module 20 further includes a feature location determining module configured to determine one or more target feature locations corresponding to the two-dimensional image based at least in part on the plurality of three-dimensional model parameters. In some examples, the deviation determining module 24 is configured to determine one or more location deviations between the one or more target feature locations and the one or more reference feature locations.

In some embodiments, the system 10 and/or the training module 20 further includes a distribution generating module configured to generate, by a distribution generating model, a target distribution of a target latent vector based at least in part on the plurality of three-dimensional model parameters. In various examples, the target latent vector corresponds to the plurality of three-dimensional model parameters. In some examples, the deviation determining module 24 is configured to determine a target distribution divergence (e.g., a Kullback-Leibler divergence) of the target distribution from the normal distribution. In certain examples, the system 10 and/or the training module 20 further includes a distribution model trainer configured to train the distribution generating model by at least: receiving one or more training parameters corresponding to a reference image of a patient having a realistic shape and/or a realistic pose; generating, by the distribution generating model, a training distribution of a training latent vector based at least in part on the one or more training parameters; determining a training distribution divergence (e.g., Kullback-Leibler divergence) of the training distribution from the normal distribution; and changing one or more parameters of the distribution generating model based at least in part on the training distribution divergence. In various examples, changing one or more parameters of the distribution generating model based at least in part on the training distribution divergence includes changing one or more parameters of the distribution generating model to reduce (e.g., minimize) the training distribution divergence.

In some examples, the distribution model trainer is configured to incorporate a set of prior (pre-determined) shape and pose parameters which correspond to realistic patient (e.g., human) configurations. In certain examples, the distribution model trainer is configured to train the distribution generating model to learn the realistic shape and pose parameters such that the underlying latent space that is being modeled (e.g., when the patient representation model is implemented), is constrained to follow one or more prior distributions corresponding to the realistic shape and pose parameters. In various examples, using such a distribution model trainer help the patient representation model to produce estimates reflecting realistic human configurations (e.g., shape, size, and pose configurations).

In various embodiments, the parameter changing module 26 is configured to change, such as based at least in part on the deviation, one or more parameters of the patient representation model. In certain examples, the parameter changing module 26 is configured to change one or more parameters of the patient representation model to reduce (e.g., minimize) the deviation. In some examples, the parameter changing module 26 is configured to change, based at least in part on the deviation, one or more parameters of the first feature extraction model, of the second feature extraction model, and/or of the parameter determining model. In certain examples, the parameter changing module 26 is configured to change one or more parameters of the first feature extraction model, of the second feature extraction model, and/or of the parameter determining model to reduce (e.g., minimize) the deviation.

In some examples, the parameter changing module 26 is configured to change, based at least in part on the deviation distance, one or more parameters of the first feature extraction model, of the second feature extraction model, and/or of the parameter determining model. In certain examples, the parameter changing module 26 is configured to change one or more parameters of the first feature extraction model, of the second feature extraction model, and/or of the parameter determining model to reduce (e.g., minimize) the deviation distance.

In various examples, the parameter changing module 26 is configured to change, based at least in part on the one or more depth deviations, one or more parameters of the first feature extraction model, of the second feature extraction model, and/or of the parameter determining model. In certain examples, the parameter changing module 26 is configured to change one or more parameters of the first feature extraction model, of the second feature extraction model, and/or of the parameter determining model to reduce (e.g., minimize) the one or more depth deviations.

In certain examples, the parameter changing module 26 is configured to change, based at least in part on the target distribution divergence, one or more parameters of the first feature extraction model, of the second feature extraction model, and/or of the parameter determining model. In certain examples, the parameter changing module 26 is configured to change one or more parameters of the first feature extraction model, of the second feature extraction model, and/or of the parameter determining model to reduce (e.g., minimize) the target distribution divergence.

In various examples, the parameter changing module 26 is configured to change, based at least in part on the one or more location deviations, one or more parameters of the first feature extraction model, of the second feature extraction model, and/or of the parameter determining model. In certain examples, the parameter changing module 26 is configured to change one or more parameters of the first feature extraction model, of the second feature extraction model, and/or of the parameter determining model to reduce (e.g., minimize) the one or more location deviations.

Figure 2:
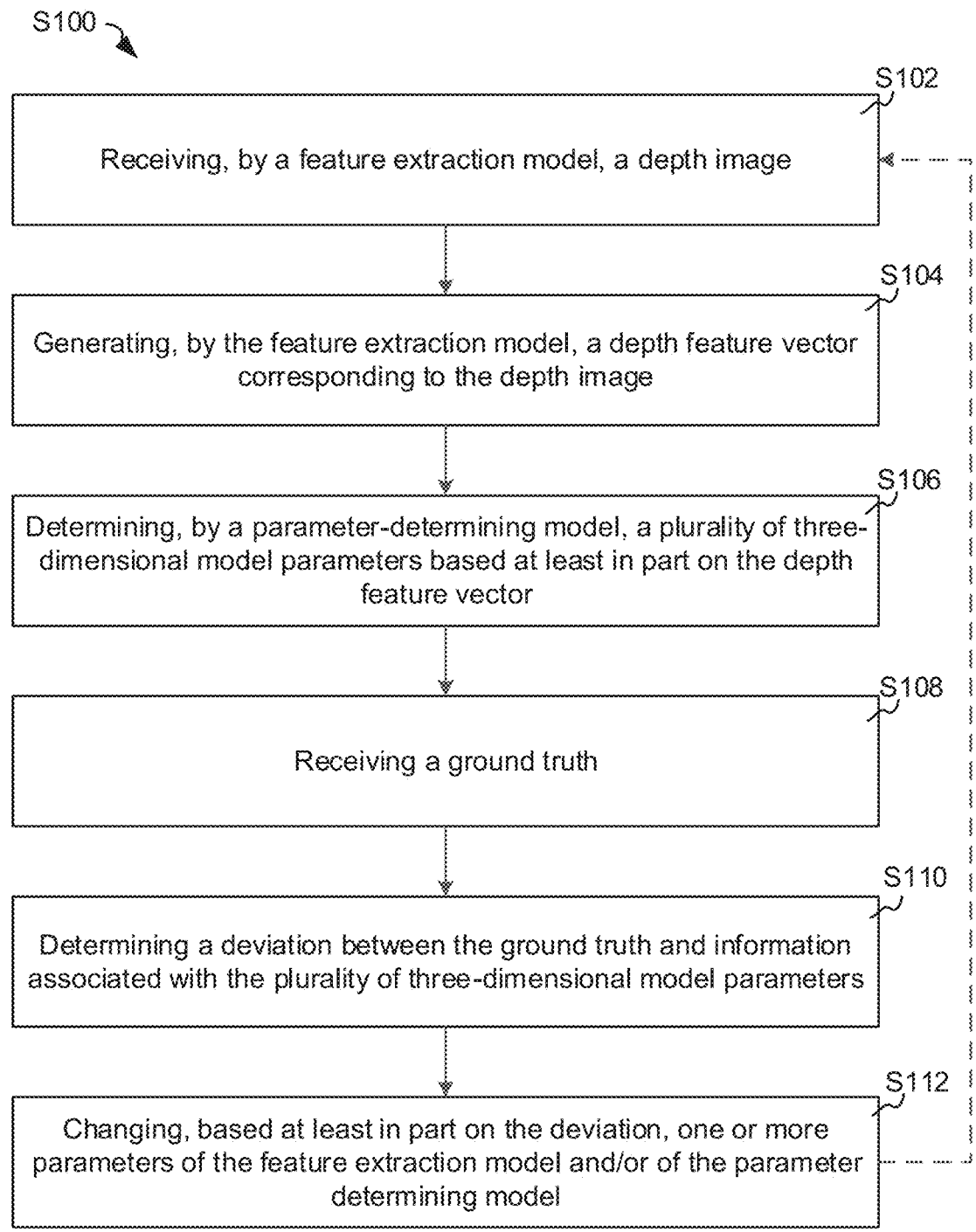
FIG. 2 is a simplified diagram showing a method for training a model for providing medical guidance, according to some embodiments.

FIG. 2 is a simplified diagram showing a method for training a patient representation model for providing medical guidance, according to some embodiments. This diagram is merely an example, which should not unduly limit the scope of the claims. One of ordinary skill in the art would recognize many variations, alternatives, and modifications. In some examples, the method S100 includes a process S102 of receiving a depth image, a process S104 of generating a depth feature vector, a process S106 of determining a plurality of three-dimensional model parameters, a process S108 of receiving a ground truth, a process S110 of determining a deviation, and a process S112 of changing one or more parameters of the patient representation model. In some examples, the method S100 is performed by one or more processors, such as using a machine learning model. In certain examples, the method S100 is for training the patient representation model used or controlled by system 10 of FIG. 1. For example, the patient representation model includes one or more feature extraction models and a parameter determining model. Although the above has been shown using a selected group of processes for the method, there can be many alternatives, modifications, and variations. For example, some of the processes may be expanded and/or combined. Other processes may be inserted to those noted above. Some processes may be removed. Depending upon the embodiment, the sequence of processes may be interchanged with others replaced.

In various embodiments, the process S102 of receiving a depth image includes receiving, by the feature extraction model, the depth image. In certain examples, the depth image is a patient image pre-analyzed for training purposes. In some examples, receiving the depth image includes inputting the depth image into the feature extraction model.

In various embodiments, the process S104 of generating a depth feature vector includes generating, by the feature extraction model, a depth feature vector corresponding to the depth image.

In various embodiments, the process S106 of determining a plurality of three-dimensional model parameters includes determining, by a parameter-determining model, a plurality of three-dimensional model parameters based at least in part on the depth feature vector.

In various embodiments, a process S108 of receiving a ground truth includes the receiving a plurality of ground truth model parameters corresponding to the depth image, one or more reference feature depths corresponding to the depth image, and/or a normal distribution.

In various embodiments, a process S110 of determining a deviation includes determining a deviation between the ground truth and information associated with the plurality of three-dimensional model parameters. In certain examples, determining the deviation includes determining a deviation distance between the plurality of three-dimensional model parameters and the plurality of ground truth model parameters. In some examples, determining the deviation includes determining one or more depth deviations between the one or more target feature depths and the one or more reference feature depths. In various examples, determining a deviation includes determining a target distribution divergence of the target distribution from the normal distribution.

In various embodiments, a process S112 of changing one or more parameters of the patient representation model includes changing one or more parameters, based at least in part on the deviation, one or more parameters of the feature extraction model and/or of the parameter determining model. In some examples, changing, based at least in part on the deviation, one or more parameters of the patient representation model includes changing, based at least in part on the deviation distance, one or more parameters of the feature extraction model and/or of the parameter determining model. In some examples, the method S100 further includes determining one or more target feature depths corresponding to the depth image based at least in part on the three-dimensional model parameters. In various examples, changing, based at least in part on the deviation, one or more parameters of the patient representation model includes changing, based at least in part on the one or more depth deviations, one or more parameters of the feature extraction model and/or of the parameter determining model. In certain examples, the method S100 further includes generating, by a distribution generating model, a target distribution of a target latent vector based at least in part on the plurality of three-dimensional model parameters. In some examples, changing, based at least in part on the deviation, one or more parameters of the patient representation model includes changing, based at least in part on the target distribution divergence, one or more parameters of the feature extraction model and/or of the parameter determining model.

In certain embodiments, changing, based at least in part on the one or more location deviations, one or more parameters of the feature extraction model, and/or of the parameter determining model includes changing one or more parameters of the feature extraction model, and/or of the parameter determining model to reduce (e.g., minimize) the deviation, the deviation distance, the one or more depth deviations, and/or the target distribution divergence.

In some embodiments, the method S100 further includes training the distribution generating model by at least: receiving one or more training parameters corresponding to a reference image of a patient having a realistic shape and/or a realistic pose; generating, by the distribution generating model, a training distribution of a training latent vector based at least in part on the one or more training parameters; determining a training distribution divergence of the training distribution from the normal distribution; and changing one or more parameters of the distribution generating model based at least in part on the training distribution divergence. In some examples, changing one or more parameters of the distribution generating model based at least in part on the training distribution divergence includes changing one or more parameters of the distribution generating model to reduce the training distribution divergence. In certain examples, determining a training distribution divergence of the training distribution from the normal distribution includes determining a Kullback-Leibler divergence.

In certain embodiments, the process S112 of changing one or more parameters of the patient representation model includes changing one or more weights and/or biases of the patient representation model, such as according to one or more gradients and/or a back-propagation process. In various embodiments, the process S112 of changing one or more parameters of the patient representation model includes repeating one or more of processes S102, S104, S106, S108, S110, and S112.

Figure 3:
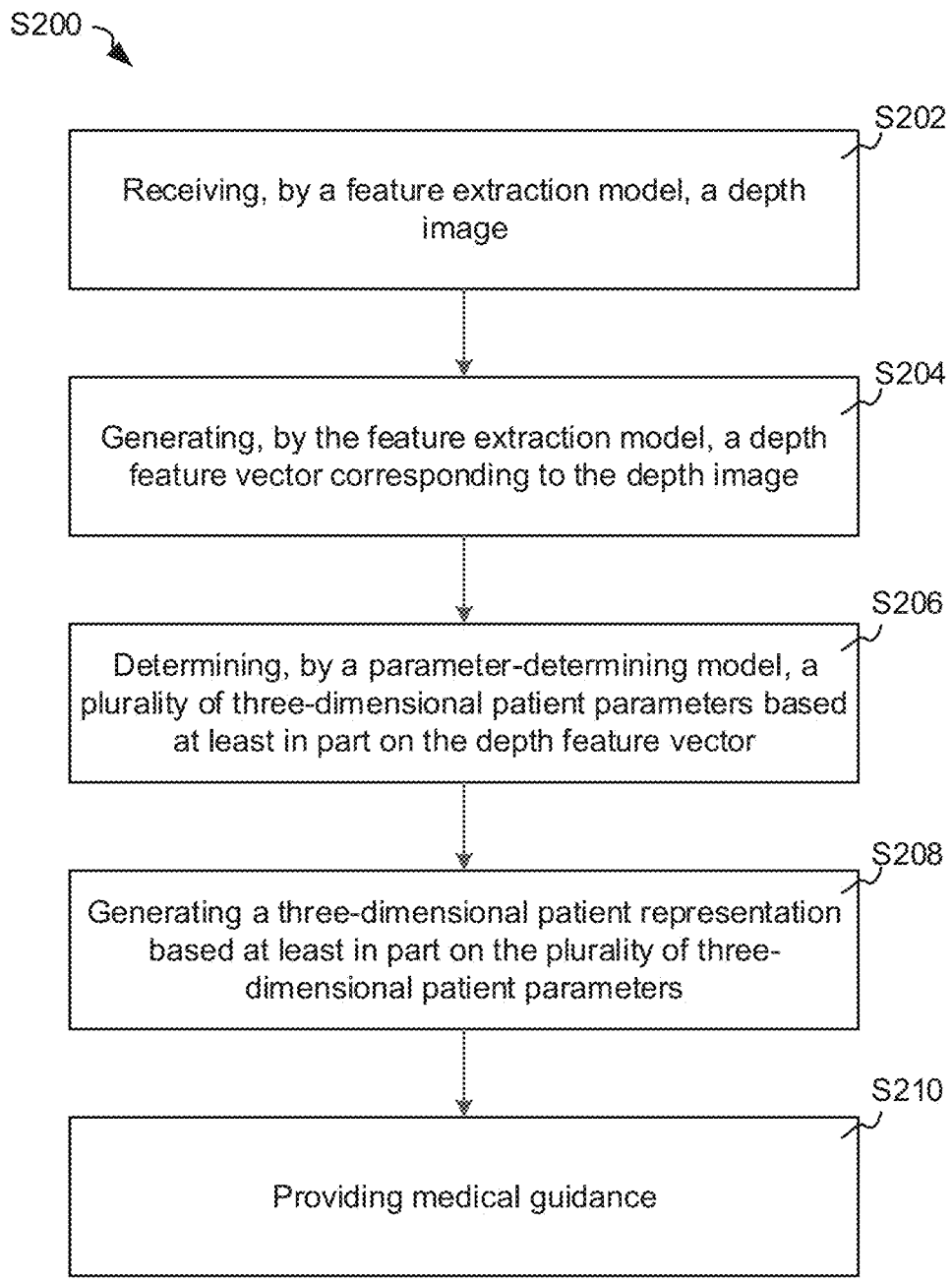
FIG. 3 is a simplified diagram showing a method for providing medical guidance, according to some embodiments.

FIG. 3 is a simplified diagram showing a method for providing medical guidance, according to some embodiments. This diagram is merely an example, which should not unduly limit the scope of the claims. One of ordinary skill in the art would recognize many variations, alternatives, and modifications. In some examples, the method S200 includes a process S102 of receiving a depth image, a process S204 of generating a depth feature vector, a process S206 of determining a plurality of three-dimensional model parameters, a process S208 of generating a three-dimensional patient representation, and a process S210 of providing medical guidance. In some examples, the method S200 is performed by one or more processors, such as using a machine learning model. In certain examples, the method S200 is configured to be implemented by system 10 of FIG. 1. For example, the system 10 is configured to implement the method S200 to use the patient representation model including one or more feature extraction models and a parameter determining model, for medical use. Although the above has been shown using a selected group of processes for the method, there can be many alternatives, modifications, and variations. For example, some of the processes may be expanded and/or combined. Other processes may be inserted to those noted above. Some processes may be removed. Depending upon the embodiment, the sequence of processes may be interchanged with others replaced.

In various embodiments, the process S202 of receiving a depth image includes receiving, by the feature extraction model, the depth image. In certain examples, the depth image is a patient image for aiding medical diagnosis. In some examples, receiving the depth image includes inputting the depth image into the feature extraction model.

In various embodiments, the process S204 of generating a depth feature vector includes generating, by the feature extraction model, a depth feature vector corresponding to the depth image.

In various embodiments, the process S206 of determining a plurality of three-dimensional patient parameters includes determining, by a parameter-determining model, a plurality of three-dimensional patient parameters based at least in part on the depth feature vector. In some examples, the plurality of three-dimensional patient parameters includes a pose parameter and/or a shape parameter.

In various embodiments, the process S208 of generating a three-dimensional patient representation includes generating the three-dimensional patient representation based at least in part on the plurality of three-dimensional patient parameters.

In various embodiments, the process S210 of providing medical guidance includes providing the plurality of three-dimensional patient parameters as medical guidance. In certain examples, providing medical guidance includes providing the three-dimensional patient representation as medical guidance. In certain examples, the medical guidance includes guidance for medical scanner positioning, medical scanning parameters optimization; and/or medical treatment sequence planning.

In certain embodiments, the method S200 further includes acquiring the depth image using a RGBD sensor, a laser sensor, a FIR sensor, a NIR sensor, and/or a lidar sensor.

Figure 4:
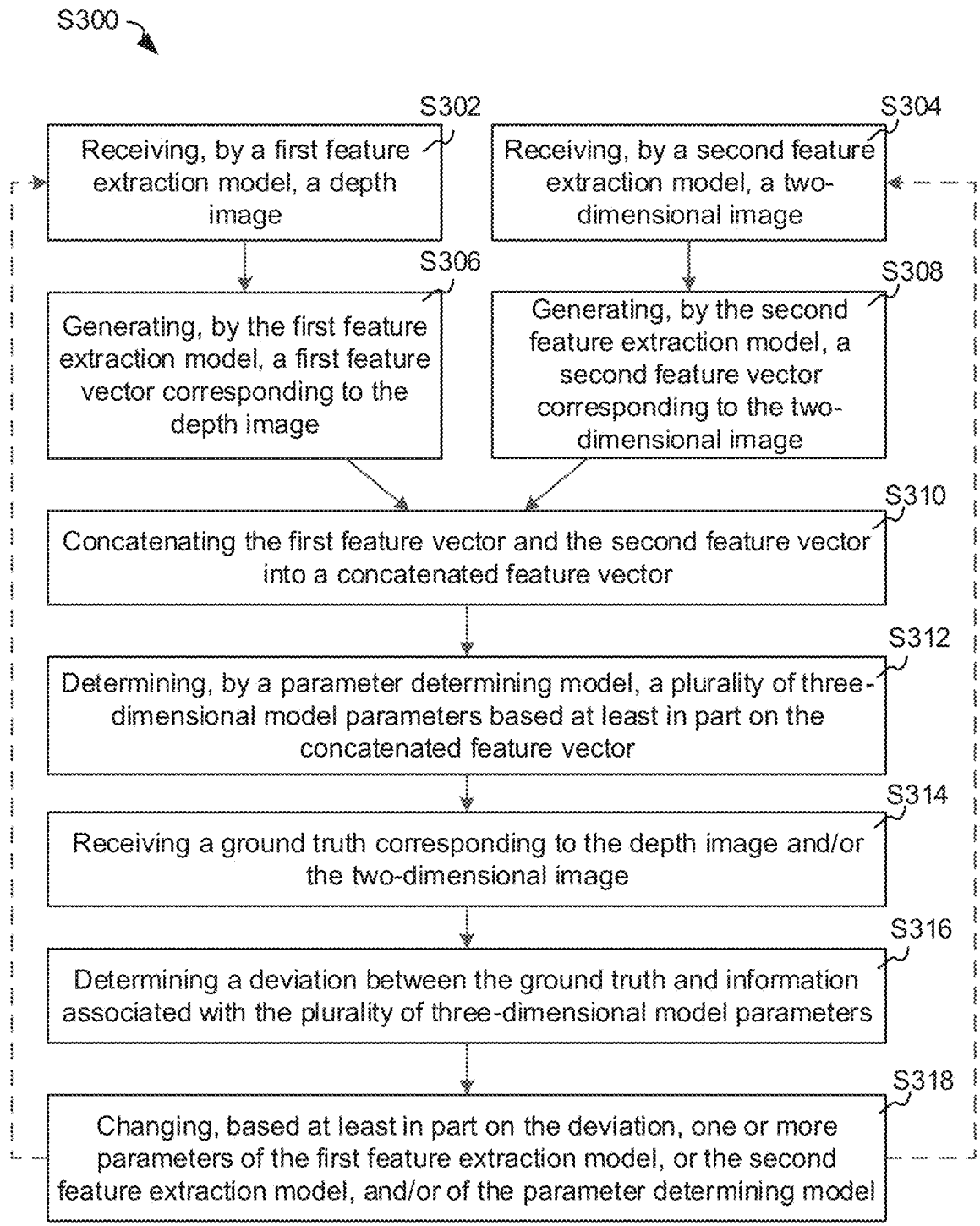
FIG. 4 is a simplified diagram showing a method for training a model for providing medical guidance, according to some embodiments.

FIG. 4 is a simplified diagram showing a method for training a patient representation model for providing medical guidance, according to some embodiments. This diagram is merely an example, which should not unduly limit the scope of the claims. One of ordinary skill in the art would recognize many variations, alternatives, and modifications. In some examples, the method S300 includes a process S302 of receiving a depth image, a process S304 of receiving a two-dimensional image, a process S306 of generating a first feature vector, a process S308 of generating a second feature vector, a process S310 of concatenating the first feature vector and the second feature vector, a process S312 of determining a plurality of three-dimensional model parameters, a process S314 of receiving a ground truth, a process S316 of determining a deviation, and a process S318 of changing one or more parameters of the patient representation model. In some examples, the method S300 is performed by one or more processors, such as using a machine learning model. In certain examples, the method S300 is for training the patient representation model used or controlled by system 10 of FIG. 1. For example, the patient representation model includes one or more feature extraction models and a parameter determining model. Although the above has been shown using a selected group of processes for the method, there can be many alternatives, modifications, and variations. For example, some of the processes may be expanded and/or combined. Other processes may be inserted to those noted above. Some processes may be removed. Depending upon the embodiment, the sequence of processes may be interchanged with others replaced.

In various embodiments, the process S302 of receiving a depth image includes receiving, by a first feature extraction model, the depth image. In certain examples, the depth image is a patient image pre-analyzed for training purposes. In some examples, receiving the depth image includes inputting the depth image into the first feature extraction model.

In various embodiments, the process S304 of receiving a two-dimensional image includes receiving, by a second feature extraction model, the two-dimensional image. In certain examples, the two-dimensional image is a patient image pre-analyzed for training purposes. In some examples, receiving the two-dimensional image includes inputting the two-dimensional image into the second feature extraction model.

In various embodiments, the process S306 of generating a first feature vector includes generating, by the first feature extraction model, the first feature vector corresponding to the depth image.

In various embodiments, the process S308 of generating a second feature vector includes generating, by the second feature extraction model, the second feature vector corresponding to the two-dimensional image.

In various embodiments, the process S310 of concatenating the first feature vector includes and the second feature vector includes concatenating the first feature vector and the second feature vector into a concatenated feature vector.

In various embodiments, the process S312 of determining a plurality of three-dimensional model parameters includes determining, by a parameter determining model, the plurality of three-dimensional model parameters based at least in part on the concatenated feature vector.

In various embodiments, the process S314 of receiving a ground truth includes receiving the ground truth corresponding to the depth image and/or the two-dimensional image. In some examples, receiving a ground truth includes receiving a plurality of ground truth model parameters corresponding to the depth image and/or the two-dimensional image. In certain examples, receiving a ground truth includes receiving one or more reference feature locations corresponding to the two-dimensional image. In various examples, receiving a ground truth includes receiving one or more reference feature depths corresponding to the depth image. In some examples, receiving a ground truth includes receiving a normal distribution.

In various examples, the method S300 further includes determining one or more target feature locations corresponding to the two-dimensional image based at least in part on the plurality of three-dimensional model parameters. In some examples, the method S300 further includes determining one or more target feature depths corresponding to the depth image based at least in part on the three-dimensional model parameters. In some examples, the method S300 further includes generating, by a distribution generating model, a target distribution of a target latent vector based at least in part on the plurality of three-dimensional model parameters In various embodiments, the process S316 of determining a deviation includes determining the deviation between the ground truth and information associated with the plurality of three-dimensional model parameters. In some examples, determining a deviation includes determining a deviation distance between the plurality of three-dimensional model parameters and the plurality of ground truth model parameters. In certain examples, determining a deviation includes determining one or more location deviations between the one or more target feature locations and the one or more reference feature locations. In various examples, determining a deviation includes determining one or more depth deviations between the one or more target feature depths and the one or more reference feature depths. In some examples, determining a deviation includes determining a target distribution divergence of the target distribution from the normal distribution.

In various embodiments, the process S318 of changing one or more parameters of the patient representation model includes changing, based at least in part on the deviation, one or more parameters of the first feature extraction model, of the second feature extraction model, and/or of the parameter determining model. In some examples, changing, based at least in part on the deviation, one or more parameters of the first feature extraction model, of the second feature extraction model, and/or of the parameter determining model includes changing, based at least in part on the deviation distance, one or more parameters of the first feature extraction model, of the second feature extraction model, and/or of the parameter determining model. In certain examples, changing, based at least in part on the deviation distance, one or more parameters of the first feature extraction model, of the second feature extraction model, and/or of the parameter determining model includes changing one or more parameters of the first feature extraction model, of the second feature extraction model, and/or of the parameter determining model to reduce (e.g., minimize) the deviation distance.

In various examples, changing, based at least in part on the deviation, one or more parameters of the first feature extraction model, of the second feature extraction model, and/or of the parameter determining model includes changing, based at least in part on the one or more location deviations, one or more parameters of the first feature extraction model, of the second feature extraction model, and/or of the parameter determining model. In some examples, changing, based at least in part on the one or more location deviations, one or more parameters of the first feature extraction model, of the second feature extraction model, and/or of the parameter determining model includes changing one or more parameters of the first feature extraction model, of the second feature extraction model, and/or of the parameter determining model to reduce (e.g., minimize) the one or more location deviations.

In some examples, changing, based at least in part on the deviation, one or more parameters of the first feature extraction model, of the second feature extraction model, and/or of the parameter determining model includes changing, based at least in part on the one or more depth deviations, one or more parameters of the first feature extraction model, of the second feature extraction model, and/or of the parameter determining model. In certain examples, changing, based at least in part on the one or more depth deviations, one or more parameters of the first feature extraction model, of the second feature extraction model, and/or of the parameter determining model includes changing one or more parameters of the first feature extraction model, of the second feature extraction model, and/or of the parameter determining model to reduce (e.g., minimize) the one or more depth deviations.

In some examples, changing, based at least in part on the deviation, one or more parameters of the first feature extraction model, of the second feature extraction model, and/or of the parameter determining model includes changing, based at least in part on the target distribution divergence, one or more parameters of the first feature extraction model, of the second feature extraction model, and/or of the parameter determining model. In various examples, changing, based at least in part on the target distribution divergence, one or more parameters of the first feature extraction model, of the second feature extraction model, and/or of the parameter determining model includes changing, one or more parameters of the first feature extraction model, of the second feature extraction model, and/or of the parameter determining model to reduce (e.g., minimize) the target distribution divergence.

In certain embodiments, the process S318 of changing one or more parameters of the patient representation model includes changing one or more weights and/or biases of the patient representation model, such as according to one or more gradients and/or a back-propagation process. In various embodiments, the process S318 of changing one or more parameters of the patient representation model includes repeating one or more of processes S302, S304, S306, S308, S310, S312, S314, S316, and S318.

In certain embodiments, the method S300 further includes training the distribution generating model by at least: receiving one or more training parameters corresponding to a reference image of a patient having a realistic shape and/or a realistic pose; generating, by the distribution generating model, a training distribution of a training latent vector based at least in part on the one or more training parameters; determining a training distribution divergence of the training distribution from the normal distribution; and changing one or more parameters of the distribution generating model based at least in part on the training distribution divergence. In some examples, changing one or more parameters of the distribution generating model based at least in part on the training distribution divergence includes changing one or more parameters of the distribution generating model to reduce the training distribution divergence. In certain examples, determining a training distribution divergence of the training distribution from the normal distribution includes determining a Kullback-Leibler divergence.

Figure 5:
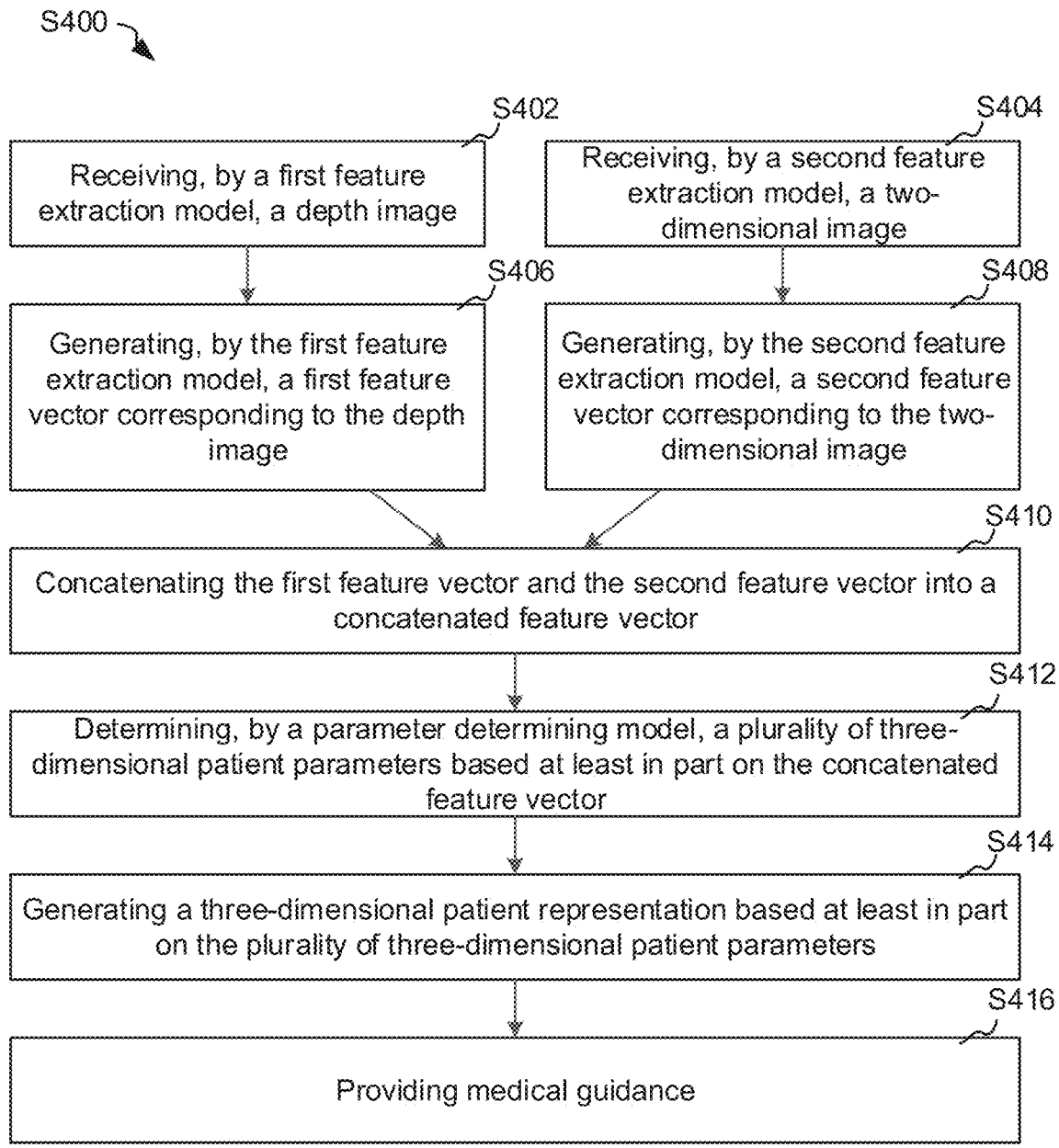
FIG. 5 is a simplified diagram showing a method for providing medical guidance, according to some embodiments.

FIG. 5 is a simplified diagram showing a method for providing medical guidance, according to some embodiments. This diagram is merely an example, which should not unduly limit the scope of the claims. One of ordinary skill in the art would recognize many variations, alternatives, and modifications. In some examples, the method S400 includes a process S402 of receiving a depth image, a process S404 of receiving a two-dimensional image, a process S406 of generating a first feature vector, a process S408 of generating a second feature vector, a process S410 of concatenating the first feature vector and the second feature vector, a process S412 of determining a plurality of three-dimensional model parameters, a process S414 of generating a three-dimensional patient representation, and a process S416 of providing medical guidance. In some examples, the method S400 is performed by one or more processors, such as using a machine learning model. In certain examples, the method S400 is configured to be implemented by system 10 of FIG. 1. For example, the system 10 is configured to implement the method S400 to use the patient representation model including one or more feature extraction models and a parameter determining model, for medical use. Although the above has been shown using a selected group of processes for the method, there can be many alternatives, modifications, and variations. For example, some of the processes may be expanded and/or combined. Other processes may be inserted to those noted above. Some processes may be removed. Depending upon the embodiment, the sequence of processes may be interchanged with others replaced.

In various embodiments, the process S402 of receiving a depth image includes receiving, by a first feature extraction model, the depth image. In certain examples, the depth image is a patient image for aiding medical diagnosis. In some examples, receiving the depth image includes inputting the depth image into the first feature extraction model.

In various embodiments, the process S404 of receiving a two-dimensional image includes receiving, by a second feature extraction model, the two-dimensional image. In certain examples, the two-dimensional image is a patient image for aiding medical diagnosis. In some examples, receiving the two-dimensional image includes inputting the two-dimensional image into the second feature extraction model.

In various embodiments, the process S406 of generating a first feature vector includes generating, by the first feature extraction model, the first feature vector corresponding to the depth image.

In various embodiments, the process S408 of generating a second feature vector includes generating, by the second feature extraction model, the second feature vector corresponding to the two-dimensional image.

In various embodiments, the process S410 of concatenating the first feature vector includes and the second feature vector includes concatenating the first feature vector and the second feature vector into a concatenated feature vector.

In various embodiments, the process S412 of determining a plurality of three-dimensional patient parameters includes determining, by a parameter determining model, the plurality of three-dimensional model parameters based at least in part on the concatenated feature vector. In some examples, the plurality of three-dimensional patient parameters includes a pose parameter and/or a shape parameter.

In various embodiments, the process S414 of generating a three-dimensional patient representation includes generating the three-dimensional patient representation based at least in part on the plurality of three-dimensional patient parameters.

In various embodiments, the process S416 of providing medical guidance includes providing the plurality of three-dimensional patient parameters as medical guidance. In certain examples, providing medical guidance includes providing the three-dimensional patient representation as medical guidance. In certain examples, the medical guidance includes guidance for medical scanner positioning, medical scanning parameters optimization; and/or medical treatment sequence planning.

In certain embodiments, the method S400 further includes acquiring the depth image using a RGBD sensor, a laser sensor, a FIR sensor, a NIR sensor, and/or a lidar sensor.

Figure 6:
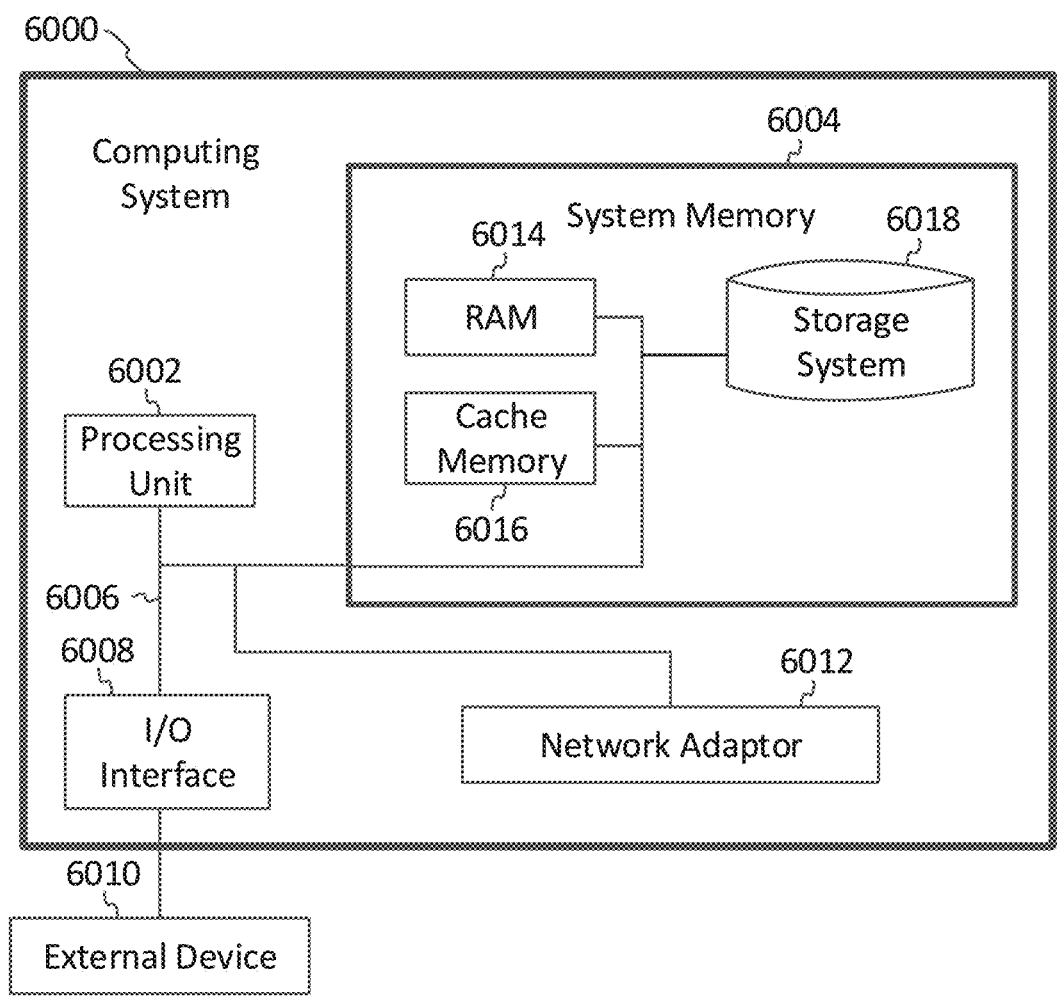
FIG. 6 is a simplified diagram showing a computing system, according to some embodiments.

FIG. 6 is a simplified diagram showing a computing system, according to some embodiments. This diagram is merely an example, which should not unduly limit the scope of the claims. One of ordinary skill in the art would recognize many variations, alternatives, and modifications. In certain examples, the computing system 6000 is a general-purpose computing device. In some examples, the computing system 6000 includes one or more processing units 6002 (e.g., one or more processors), one or more system memories 6004, one or more buses 6006, one or more input/output (I/O) interfaces 6008, and/or one or more network adapters 6012. In certain examples, the one or more buses 6006 connect various system components including, for example, the one or more system memories 6004, the one or more processing units 6002, the one or more input/output (I/O) interfaces 6008, and/or the one or more network adapters 6012. Although the above has been shown using a selected group of components for the computing system, there can be many alternatives, modifications, and variations. For example, some of the components may be expanded and/or combined. Other components may be inserted to those noted above. Some components may be removed. Depending upon the embodiment, the arrangement of components may be interchanged with others replaced.

In certain examples, the computing system 6000 is a computer (e.g., a server computer, a client computer), a smartphone, a tablet, or a wearable device. In some examples, some or all processes (e.g., steps) of the method S100, the method S200, the method S300, and/or the method S400 are performed by the computing system 6000. In certain examples, some or all processes (e.g., steps) of the method S100, the method S200, the method S300, and/or the method S400 are performed by the one or more processing units 6002 directed by one or more codes. For example, the one or more codes are stored in the one or more system memories 6004 (e.g., one or more non-transitory computer-readable media), and are readable by the computing system 6000 (e.g., readable by the one or more processing units 6002). In various examples, the one or more system memories 6004 include one or more computer-readable media in the form of volatile memory, such as a random-access memory (RAM) 6014, a cache memory 6016, and/or a storage system 6018 (e.g., a floppy disk, a CD-ROM, and/or a DVD-ROM).

In some examples, the one or more input/output (I/O) interfaces 6008 of the computing system 6000 is configured to be in communication with one or more external devices 6010 (e.g., a keyboard, a pointing device, and/or a display). In certain examples, the one or more network adapters 6012 of the computing system 6000 is configured to communicate with one or more networks (e.g., a local area network (LAN), a wide area network (WAN), and/or a public network (e.g., the Internet)). In various examples, additional hardware and/or software modules are utilized in connection with the computing system 6000, such as one or more micro-codes and/or one or more device drivers.

In various examples, the feature extraction model, the first feature extraction model, the second feature extraction model, the parameter determining model, and/or the distribution determining mode, is a neural network, such as a deep neural network, such as a convolutional neural network.

Figure 7:
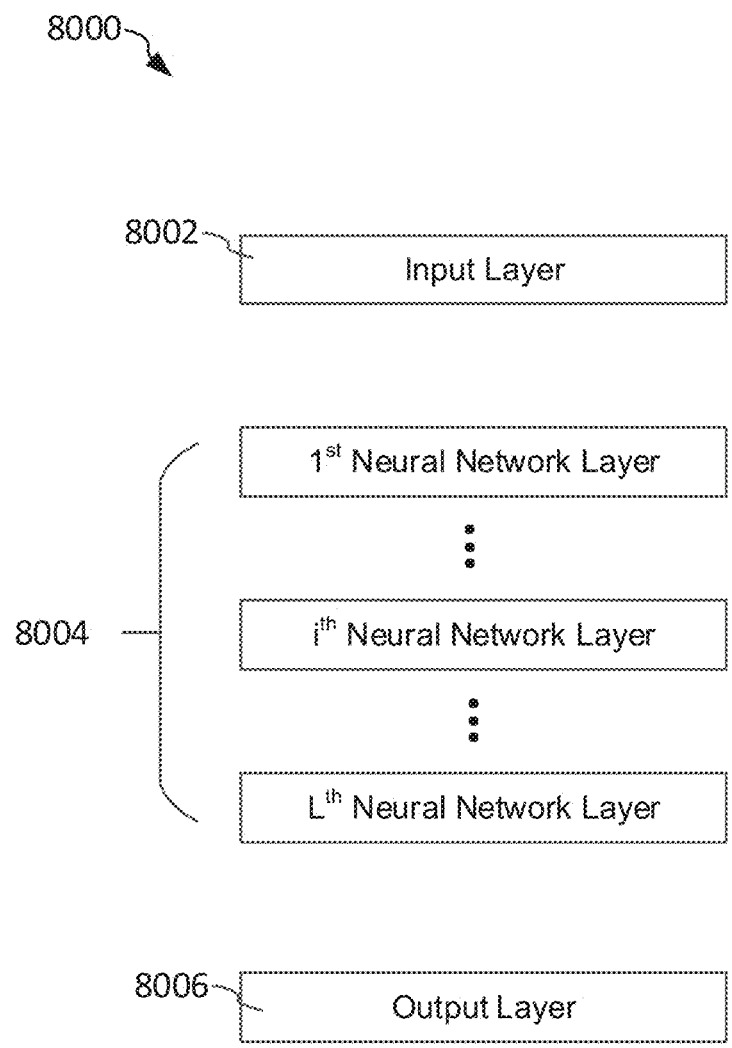
FIG. 7 is a simplified diagram showing a neural network, according to some embodiments.

FIG. 7 is a simplified diagram showing a neural network, according to certain embodiments. This diagram is merely an example, which should not unduly limit the scope of the claims. One of ordinary skill in the art would recognize many variations, alternatives, and modifications. The neural network 8000 is an artificial neural network. In some examples, the neural network 8000 includes an input layer 8002, one or more hidden layers 8004, and an output layer 8006. For example, the one or more hidden layers 8004 includes L number of neural network layers, which include a $1^{st}$ neural network layer, . . . , an $i^{th}$ neural network layer, . . . and an $L^{th}$ neural network layer, where L is a positive integer and i is an integer that is larger than or equal to 1 and smaller than or equal to L. Although the above has been shown using a selected group of components for the neural network, there can be many alternatives, modifications, and variations. For example, some of the components may be expanded and/or combined. Other components may be inserted to those noted above. Some components may be removed. Depending upon the embodiment, the arrangement of components may be interchanged with others replaced.

In some examples, some or all processes (e.g., steps) of the method S100, the method S200, the method S300, and/or the method S400 are performed by the neural network 8000 (e.g., using the computing system 6000). In certain examples, some or all processes (e.g., steps) of the method S100, the method S200, the method S300, and/or the method S400 are performed by the one or more processing units 6002 directed by one or more codes that implement the neural network 8000. For example, the one or more codes for the neural network 8000 are stored in the one or more system memories 6004 (e.g., one or more non-transitory computer-readable media), and are readable by the computing system 6000 such as by the one or more processing units 6002.

In certain examples, the neural network 8000 is a deep neural network (e.g., a convolutional neural network). In some examples, each neural network layer of the one or more hidden layers 8004 includes multiple sublayers. As an example, the $i^{th}$ neural network layer includes a convolutional layer, an activation layer, and a pooling layer. For example, the convolutional layer is configured to perform feature extraction on an input (e.g., received by the input layer or from a previous neural network layer), the activation layer is configured to apply a nonlinear activation function (e.g., a ReLU function) to the output of the convolutional layer, and the pooling layer is configured to compress (e.g., to down-sample, such as by performing max pooling or average pooling) the output of the activation layer. As an example, the output layer 8006 includes one or more fully connected layers.

As discussed above and further emphasized here, FIG. 7 is merely an example, which should not unduly limit the scope of the claims. One of ordinary skill in the art would recognize many variations, alternatives, and modifications. For example, the neural network 8000 is replaced by an algorithm that is not an artificial neural network. As an example, the neural network 8000 is replaced by a machine learning model that is not an artificial neural network.

Figure 8:
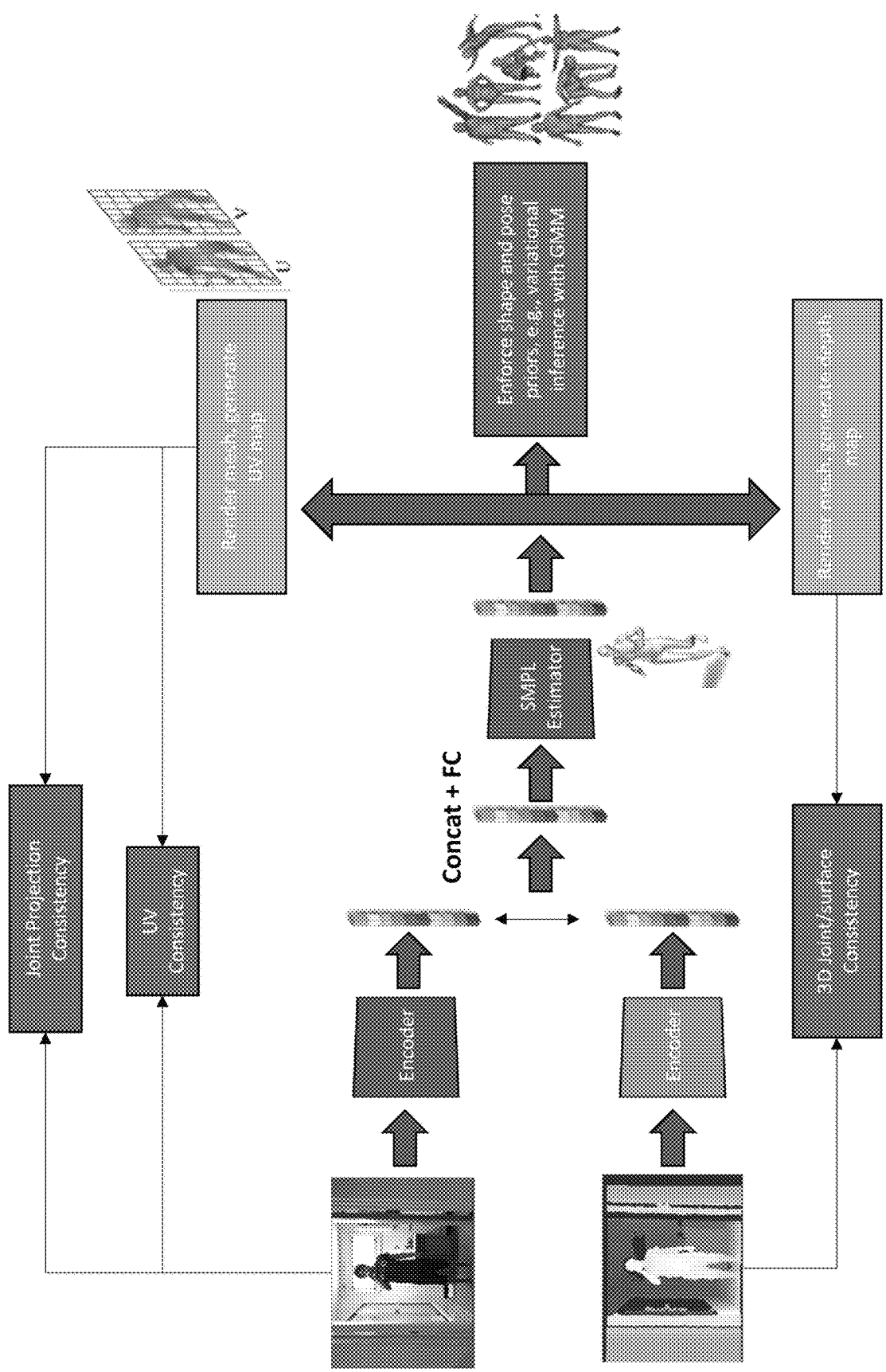
FIG. 8 is a simplified diagram showing a patient representation estimation process, according to some embodiments.

FIG. 8 is a simplified diagram showing a patient representation estimation process, according to some embodiments. In certain examples, the patient representation estimation process is configured to be implemented by the system 10 of FIG. 1 and may be implemented, at least partly, according to the method S100 of FIG. 2, the method S200 of FIG. 3, the method S300 of FIG. 4, and/or the method S400 of FIG. 5. In some examples, the patient representation estimation imposes a joint projection consistency constraint. In certain embodiments, the methods and systems of the present disclosure are configured to reduce depth ambiguity in providing patient representation as medical guidance. In some examples, consistency constraints relating to realistic patient configurations (e.g., pose, shape, size) are explicitly enforced as backward and forward projection consistency constraints. In various examples, the methods and systems are configured to receive a patient image (e.g., RGB or depth), fit a three-dimensional model corresponding to the patient image, where the three-dimensional model having estimated model parameters. Based on the model parameters, the systems and methods are configured to render three-dimensional feature (e.g., joint) locations and re-project the feature (joint) onto the patient image. In some examples, the systems and methods are configured to improve accuracy through training to reduce (e.g., minimize) the reprojection error between the actual locations of the two-dimensional joints and the re-projected locations of the two-dimensional joints. In certain examples, the systems and methods are configured to, with such a consistency constraint, to estimate only the one, and correct, three-dimensional patient configuration that correlates (e.g., explains) the given patient image.

In certain embodiments, the patient representation estimation process further enforces surface consistency constraint to further reduce the depth ambiguity. In some examples, enforcing the surface consistency constraint includes imposing a constraint between a rendered depth map and an input depth map to force the surface rendered from the estimated parameters is similar (e.g., substantially similar) to the input surface.

In certain embodiments, systems and methods implement one or more machine learning models (e.g., neural networks) to obtain realistic three-dimensional patient configurations fitting to realistic fitted models of a patient's body that corresponds to a given patient image. In certain examples, one or more of the machine learning models is trained and regularized to produce only realistic configurations (e.g., patient shape and/or patient pose).

In certain embodiments, such as to ensure realistic outputs of shapes and poses, one or more of the machine learning models are trained by enforcing realistic shape and pose priors on the estimated parameters. In certain examples, training a machine learning model includes fitting a Gaussian mixture model (GMM) to a large collection of synthetic, realistic human bodies, and obtaining the GMM for both shape and pose parameters. In some examples, a distribution is used to enforce a variational objective on the estimated model parameters during training to effectively ensure the estimated parameters also follow the same distribution as the prior distribution.

In certain embodiments, the training process further includes enforcing the requirement that the estimated shape and pose parameters result in the same UV parameterization as the original, input RGB image. In certain examples, based at least in part on the estimated model shape and pose parameters, the training process includes rendering the model vertices to determine the UV mapping, seeking and regularize the learning process by explicitly enforcing the estimated UV mapping to be consistent with the UV mapping of the input image, such as via a UV estimator.

In certain embodiments, one or more of the machine learning models is trained with at least the following objectives: joint projection consistency, UV consistency, three-dimensional surface consistency, and variational parameter optimization. In certain embodiments, a system and/or a method implementing the trained one or more machine learning models is configured to receive a set of two-dimensional patient images (e.g., RGB, depth), run inference with the trained machine learning model, and estimate the patient model parameters. In certain embodiments, the patient model parameters are used for downstream tasks such as scanner parameter optimization, scanner positioning, and/or treatment planning.

In various embodiments, a computer-implemented method for providing medical guidance using a patient representation model (e.g., a model including one or more feature extraction models and a parameter determining model) includes: receiving, by a first feature extraction model, a depth image; generating, by the first feature extraction model, a first feature vector corresponding to the depth image; determining, by a parameter determining model, a plurality of three-dimensional model parameters based at least in part on the first feature vector; receiving a ground truth; determining a deviation between the ground truth and information associated with the plurality of three-dimensional model parameters; changing, based at least in part on the deviation, one or more parameters of the patient representation model. In certain examples, such as after the changing one or more parameters of the patient representation model, the method further includes providing medical guidance by at least: receiving, by the first feature extraction model, a first patient image; determining, by the parameter determining model, a plurality of three-dimensional patient parameters based at least in part on the first patient image; and providing the plurality of three-dimensional patient parameters as medical guidance. In certain examples, the computer-implemented method is performed by one or more processors. In some examples, the computer-implemented method is implemented at least partly according to the method S100 of FIG. 2, the method S200 of FIG. 3, the method S300 of FIG. 4, and/or the method S400 of FIG. 5. In certain examples, the method is implemented at least partly by the system 10 of FIG. 1.

In some embodiments, the receiving a ground truth includes receiving a plurality of ground truth model parameters corresponding to the depth image. In certain examples, the determining a deviation includes determining a deviation distance between the plurality of three-dimensional model parameters and the plurality of ground truth model parameters. In some examples, the changing, based at least in part on the deviation, one or more parameters of the patient representation model includes changing, based at least in part on the deviation distance, one or more parameters of the first feature extraction model and/or of the parameter determining model.

In some embodiments, the computer-implemented method further includes determining one or more target feature depths corresponding to the depth image based at least in part on the three-dimensional model parameters. In certain examples, the receiving a ground truth includes receiving one or more reference feature depths corresponding to the depth image. In some examples, the determining a deviation includes determining one or more depth deviations between the one or more target feature depths and the one or more reference feature depths. In various examples, the changing, based at least in part on the deviation, one or more parameters of the patient representation model includes changing, based at least in part on the one or more depth deviations, one or more parameters of the first feature extraction model and/or of the parameter determining model.

In some embodiments, the computer-implemented method further includes generating, by a distribution generating model, a target distribution of a target latent vector based at least in part on the plurality of three-dimensional model parameters. In certain examples, the receiving a ground truth includes receiving a normal distribution. In some examples, the determining a deviation includes determining a target distribution divergence of the target distribution from the normal distribution. In various examples, the changing, based at least in part on the deviation, one or more parameters of the patient representation model includes changing, based at least in part on the target distribution divergence, one or more parameters of the first feature extraction model and/or of the parameter determining model.

In some embodiments, the computer-implemented method further includes: receiving, by a second feature extraction model, a two-dimensional image; generating, by the second feature extraction model, a second feature vector corresponding to the two-dimensional image; and concatenating the first feature vector and the second feature vector into a concatenated feature vector. In certain examples, the determining a plurality of three-dimensional model parameters includes determining, by the parameter determining model, the plurality of three-dimensional model parameters based at least in part on the concatenated feature vector; the receiving a ground truth includes receiving a ground truth corresponding to the depth image and the two-dimensional image; the changing one or more parameters of the patient representation model includes changing, based at least in part on the deviation, one or more parameters of the first feature extraction model, of the second feature extraction model, and/or of the parameter determining model.

In some embodiments, the receiving a ground truth includes receiving a plurality of ground truth model parameters corresponding to the depth image and the two-dimensional image. In certain examples, the determining a deviation includes determining a deviation distance between the plurality of three-dimensional model parameters and the plurality of ground truth model parameters. In some examples, the changing, based at least in part on the deviation, one or more parameters of the first feature extraction model, of the second feature extraction model, and/or of the parameter determining model includes changing, based at least in part on the deviation distance, one or more parameters of the first feature extraction model, of the second feature extraction model, and/or of the parameter determining model.

In some embodiments, the changing, based at least in part on the deviation distance, one or more parameters of the first feature extraction model, of the second feature extraction model, and/or of the parameter determining model includes changing one or more parameters of the first feature extraction model, of the second feature extraction model, and/or of the parameter determining model to reduce the deviation distance.

In some embodiments, the computer-implemented method further includes determining one or more target feature locations corresponding to the two-dimensional image based at least in part on the plurality of three-dimensional model parameters. In certain examples, the receiving a ground truth includes receiving one or more reference feature locations corresponding to the two-dimensional image. In some examples, the determining a deviation includes determining one or more location deviations between the one or more target feature locations and the one or more reference feature locations. In various examples, the changing, based at least in part on the deviation, one or more parameters of the first feature extraction model, of the second feature extraction model, and/or of the parameter determining model includes changing, based at least in part on the one or more location deviations, one or more parameters of the first feature extraction model, of the second feature extraction model, and/or of the parameter determining model.

In some embodiments, the changing, based at least in part on the one or more location deviations, one or more parameters of the first feature extraction model, of the second feature extraction model, and/or of the parameter determining model includes changing one or more parameters of the first feature extraction model, of the second feature extraction model, and/or of the parameter determining model to reduce the one or more location deviations.

In some embodiments, the computer-implemented method further includes determining one or more target feature depths corresponding to the depth image based at least in part on the three-dimensional model parameters. In certain examples, the receiving a ground truth includes receiving one or more reference feature depths corresponding to the depth image. In some examples, the determining a deviation includes determining one or more depth deviations between the one or more target feature depths and the one or more reference feature depths. In various examples, the changing, based at least in part on the deviation, one or more parameters of the first feature extraction model, of the second feature extraction model, and/or of the parameter determining model includes changing, based at least in part on the one or more depth deviations, one or more parameters of the first feature extraction model, of the second feature extraction model, and/or of the parameter determining model.

In some embodiments, the changing, based at least in part on the one or more depth deviations, one or more parameters of the first feature extraction model, of the second feature extraction model, and/or of the parameter determining model includes changing one or more parameters of the first feature extraction model, of the second feature extraction model, and/or of the parameter determining model to reduce the one or more depth deviations.

In some embodiments, the computer-implemented method further includes generating, by a distribution generating model, a target distribution of a target latent vector based at least in part on the plurality of three-dimensional model parameters. In certain examples, the receiving a ground truth includes receiving a normal distribution. In some examples, the determining a deviation includes determining a target distribution divergence of the target distribution from the normal distribution. In various examples, the changing, based at least in part on the deviation, one or more parameters of the first feature extraction model, of the second feature extraction model, and/or of the parameter determining model includes changing, based at least in part on the target distribution divergence, one or more parameters of the first feature extraction model, of the second feature extraction model, and/or of the parameter determining model.

In some embodiments, the changing, based at least in part on the target distribution divergence, one or more parameters of the first feature extraction model, of the second feature extraction model, and/or of the parameter determining model includes changing, one or more parameters of the first feature extraction model, of the second feature extraction model, and/or of the parameter determining model to reduce the target distribution divergence.

In some embodiments, the computer-implemented method further includes training the distribution generating model by at least: receiving one or more training parameters corresponding to a reference image of a patient having a realistic shape and/or a realistic pose; generating, by the distribution generating model, a training distribution of a training latent vector based at least in part on the one or more training parameters; determining a training distribution divergence of the training distribution from the normal distribution; and changing one or more parameters of the distribution generating model based at least in part on the training distribution divergence.

In some embodiments, the changing one or more parameters of the distribution generating model based at least in part on the training distribution divergence includes changing one or more parameters of the distribution generating model to reduce the training distribution divergence.

In some embodiments, the determining a training distribution divergence of the training distribution from the normal distribution includes determining a Kullback-Leibler divergence.

In some embodiments, the computer-implemented method further includes: generating a three-dimensional patient representation based at least in part on the plurality of three-dimensional patient parameters; and/or providing the three-dimensional patient representation as medical guidance.

In some embodiments, the plurality of three-dimensional patient parameters includes a pose parameter and/or a shape parameter. In certain examples, the medical guidance includes guidance for medical scanner positioning, medical scanning parameters optimization; and/or medical treatment sequence planning.

In various embodiments, a system for providing medical guidance using a patient representation model (e.g., a model including one or more feature extraction models and a parameter determining model) includes: an image receiving module configured to receive, by a first feature extraction model, a depth image; a feature vector generating module configured to generate, by the first feature extraction model, a first feature vector corresponding to the depth image; a parameter determining module configured to determine, by a parameter determining model, a plurality of three-dimensional patient parameters based at least in part on the first feature vector; a ground truth receiving module configured to receive a ground truth; a deviation determining module configured to determine a deviation between the ground truth and information associated with the plurality of three-dimensional model parameters; a parameter changing module configured to change, based at least in part on the deviation, one or more parameters of the patient representation model. In certain examples, the image receiving module is further configured to receive a patient image. In some examples, the parameter determining module is further configured to determine a plurality of three-dimensional patient parameters based at least in part on the first patient image. In various examples, the system further includes a guidance providing module configured to provide the plurality of three-dimensional patient parameters as medical guidance. In some examples, the system is implemented at least partly according to the system 10 of FIG. 1. In certain examples, the system is configured to perform, at least partly, the method S100 of FIG. 2, the method S200 of FIG. 3, the method S300 of FIG. 4, and/or the method S400 of FIG. 5.

In some embodiments, the ground truth receiving module is configured to receive a plurality of ground truth model parameters corresponding to the depth image. In certain examples, the deviation determining module is configured to determine a deviation distance between the plurality of three-dimensional model parameters and the plurality of ground truth model parameters. In some examples, the parameter changing module is configured to change, based at least in part on the deviation distance, one or more parameters of the first feature extraction model and/or of the parameter determining model.

In some embodiments, the system further includes a feature depth determining module configured to determine one or more target feature depths corresponding to the depth image based at least in part on the three-dimensional model parameters. In certain examples, the ground truth module is configured to receive one or more reference feature depths corresponding to the depth image. In some examples, the deviation determining module is configured to determine one or more depth deviations between the one or more target feature depths and the one or more reference feature depths. In various examples, the parameter changing module is configured to change, based at least in part on the one or more depth deviations, one or more parameters of the first feature extraction model and/or of the parameter determining model.

In some embodiments, the system further includes a distribution generating module configure to generate, by a distribution generating model, a target distribution of a target latent vector based at least in part on the plurality of three-dimensional model parameters. In certain examples, the ground truth receiving module is configured to receive a normal distribution. In some examples, the deviation determining module is configured to determine a target distribution divergence of the target distribution from the normal distribution. In various examples, the parameter changing module is configured to change, based at least in part on the target distribution divergence, one or more parameters of the first feature extraction model and/or of the parameter determining model.

In some embodiments, the image receiving module is further configured to receive, by a second feature extraction model, a two-dimensional image. In certain examples, the feature vector generating module is further configured to generate, by the second feature extraction model, a second feature vector corresponding to the two-dimensional image. In some examples, the system further includes a vector concatenating module configured to concatenate the first feature vector and the second feature vector into a concatenated feature vector. In various examples, the parameter determining module is further configured to determine, by the parameter determining model, the plurality of three-dimensional model parameters based at least in part on the concatenated feature vector. In certain examples, the ground truth receiving module is configured to receive a ground truth corresponding to the depth image and the two-dimensional image. In some examples, the parameter changing module is configured to change, based at least in part on the deviation, one or more parameters of the first feature extraction model, of the second feature extraction model, and/or of the parameter determining model.

In some embodiments, the ground truth receiving module is configured to receive a plurality of ground truth model parameters corresponding to the depth image and the two-dimensional image. In certain examples, the deviation determining module is configured to determine a deviation distance between the plurality of three-dimensional model parameters and the plurality of ground truth model parameters. In some examples, the parameter changing module is configured to change, based at least in part on the deviation distance, one or more parameters of the first feature extraction model, of the second feature extraction model, and/or of the parameter determining model.

In some embodiments, the parameter changing module is configured to change one or more parameters of the first feature extraction model, of the second feature extraction model, and/or of the parameter determining model to reduce the deviation distance.

In some embodiments, the system further includes a feature location determining module configured to determine one or more target feature locations corresponding to the two-dimensional image based at least in part on the plurality of three-dimensional model parameters. In certain examples, the ground truth receiving module is configured to receive one or more reference feature locations corresponding to the two-dimensional image. In some examples, the deviation determining module is configured to determine one or more location deviations between the one or more target feature locations and the one or more reference feature locations. In various examples, the parameter changing module is configured to change, based at least in part on the one or more location deviations, one or more parameters of the first feature extraction model, of the second feature extraction model, and/or of the parameter determining model.

In some embodiments, the parameter changing module is configured to change one or more parameters of the first feature extraction model, of the second feature extraction model, and/or of the parameter determining model to reduce the one or more location deviations.

In some embodiments, the feature depth determining module is further configured to determine one or more target feature depths corresponding to the depth image based at least in part on the three-dimensional model parameters. In certain examples, the ground truth receiving module is configured to receive one or more reference feature depths corresponding to the depth image. In some examples, the deviation determining module is further configured to determine one or more depth deviations between the one or more target feature depths and the one or more reference feature depths. In various examples, the parameter changing module is further configured to change, based at least in part on the one or more depth deviations, one or more parameters of the first feature extraction model, of the second feature extraction model, and/or of the parameter determining model.

In some embodiments, the parameter changing module is configured to change one or more parameters of the first feature extraction model, of the second feature extraction model, and/or of the parameter determining model to reduce the one or more depth deviations.

In some embodiments, the distribution generating module is further configured to generate, by the distribution generating model, a target distribution of a target latent vector based at least in part on the plurality of three-dimensional model parameters. In certain examples, the ground truth receiving module is further configured to receive a normal distribution. In some examples, the deviation determining module is configured to determine a target distribution divergence of the target distribution from the normal distribution. In various examples, parameter changing module is further configured to change, based at least in part on the target distribution divergence, one or more parameters of the first feature extraction model, of the second feature extraction model, and/or of the parameter determining model.

In some embodiments, the parameter changing module is configured to change one or more parameters of the first feature extraction model, of the second feature extraction model, and/or of the parameter determining model to reduce the target distribution divergence.

In some embodiments, the system further includes a distribution model trainer configured to train the distribution generating model by at least: receiving one or more training parameters corresponding to a reference image of a patient having a realistic shape and/or a realistic pose; generating, by the distribution generating model, a training distribution of a training latent vector based at least in part on the one or more training parameters; determining a training distribution divergence of the training distribution from the normal distribution; and changing one or more parameters of the distribution generating model based at least in part on the training distribution divergence.

In some embodiments, the changing one or more parameters of the distribution generating model based at least in part on the training distribution divergence includes changing one or more parameters of the distribution generating model to reduce the training distribution divergence.

In some embodiments, the determining a training distribution divergence of the training distribution from the normal distribution includes determining a Kullback-Leibler divergence.

In some embodiments, the guidance providing module is further configured to generate a three-dimensional patient representation based at least in part on the plurality of three-dimensional patient parameters and/or provide the three-dimensional patient representation as medical guidance.

In some embodiments, the plurality of three-dimensional patient parameters includes a pose parameter and/or a shape parameter. In certain examples, the medical guidance includes guidance for medical scanner positioning, medical scanning parameters optimization; and/or medical treatment sequence planning.

In various embodiments, a non-transitory computer-readable medium with instructions stored thereon, that when executed by a processor, causes the processor to perform one or more processes including: receiving, by a first feature extraction model, a depth image; generating, by the first feature extraction model, a first feature vector corresponding to the depth image; determining, by a parameter determining model, a plurality of three-dimensional model parameters based at least in part on the first feature vector; receiving a ground truth; determining a deviation between the ground truth and information associated with the plurality of three-dimensional model parameters; changing, based at least in part on the deviation, one or more parameters of the patient representation model. In certain examples, such as after the changing one or more parameters of the patient representation model, the non-transitory computer-readable medium with instructions stored thereon, that when executed by a processor, further causes the processor to perform: providing medical guidance by at least: receiving, by the first feature extraction model, a first patient image; determining, by the parameter determining model, a plurality of three-dimensional patient parameters based at least in part on the first patient image; and providing the plurality of three-dimensional patient parameters as medical guidance. In some examples, the non-transitory computer-readable medium with instructions stored thereon is implemented according to the method S100 of FIG. 2, the method S200 of FIG. 3, the method S300 of FIG. 4, and/or the method S400 of FIG. 5. In certain examples, the non-transitory computer-readable medium with instructions stored thereon is configured to be implemented at least partly by the system 10 (e.g., a terminal) of FIG. 1.

In some embodiments, the non-transitory computer-readable medium, that when executed by a processor, further causes the processor to perform: receiving a plurality of ground truth model parameters corresponding to the depth image; determining a deviation distance between the plurality of three-dimensional model parameters and the plurality of ground truth model parameters; and changing, based at least in part on the deviation distance, one or more parameters of the first feature extraction model and/or of the parameter determining model.

In some embodiments, the non-transitory computer-readable medium, that when executed by a processor, further causes the processor to perform: determining one or more target feature depths corresponding to the depth image based at least in part on the three-dimensional model parameters. In certain examples, the receiving a ground truth includes receiving one or more reference feature depths corresponding to the depth image. In some examples, the determining a deviation includes determining one or more depth deviations between the one or more target feature depths and the one or more reference feature depths. In various examples, the changing, based at least in part on the deviation, one or more parameters of the patient representation model includes changing, based at least in part on the one or more depth deviations, one or more parameters of the first feature extraction model and/or of the parameter determining model.

In some embodiments, the non-transitory computer-readable medium, that when executed by a processor, further causes the processor to perform: generating, by a distribution generating model, a target distribution of a target latent vector based at least in part on the plurality of three-dimensional model parameters. In certain examples, the receiving a ground truth includes receiving a normal distribution. In some examples, the determining a deviation includes determining a target distribution divergence of the target distribution from the normal distribution. In various examples, the changing, based at least in part on the deviation, one or more parameters of the patient representation model includes changing, based at least in part on the target distribution divergence, one or more parameters of the first feature extraction model and/or of the parameter determining model.

In some embodiments, the non-transitory computer-readable medium, that when executed by a processor, further causes the processor to perform: receiving, by a second feature extraction model, a two-dimensional image; generating, by the second feature extraction model, a second feature vector corresponding to the two-dimensional image; and concatenating the first feature vector and the second feature vector into a concatenated feature vector. In certain examples, the determining a plurality of three-dimensional model parameters includes determining, by the parameter determining model, the plurality of three-dimensional model parameters based at least in part on the concatenated feature vector; the receiving a ground truth includes receiving a ground truth corresponding to the depth image and the two-dimensional image; the changing one or more parameters of the patient representation model includes changing, based at least in part on the deviation, one or more parameters of the first feature extraction model, of the second feature extraction model, and/or of the parameter determining model.

In some embodiments, the receiving a ground truth includes receiving a plurality of ground truth model parameters corresponding to the depth image and the two-dimensional image. In certain examples, the determining a deviation includes determining a deviation distance between the plurality of three-dimensional model parameters and the plurality of ground truth model parameters. In some examples, the changing, based at least in part on the deviation, one or more parameters of the first feature extraction model, of the second feature extraction model, and/or of the parameter determining model includes changing, based at least in part on the deviation distance, one or more parameters of the first feature extraction model, of the second feature extraction model, and/or of the parameter determining model.

In some embodiments, the changing, based at least in part on the deviation distance, one or more parameters of the first feature extraction model, of the second feature extraction model, and/or of the parameter determining model includes changing one or more parameters of the first feature extraction model, of the second feature extraction model, and/or of the parameter determining model to reduce the deviation distance.

In some embodiments, the non-transitory computer-readable medium, that when executed by a processor, further causes the processor to perform: determining one or more target feature locations corresponding to the two-dimensional image based at least in part on the plurality of three-dimensional model parameters. In certain examples, the receiving a ground truth includes receiving one or more reference feature locations corresponding to the two-dimensional image. In some examples, the determining a deviation includes determining one or more location deviations between the one or more target feature locations and the one or more reference feature locations. In various examples, the changing, based at least in part on the deviation, one or more parameters of the first feature extraction model, of the second feature extraction model, and/or of the parameter determining model includes changing, based at least in part on the one or more location deviations, one or more parameters of the first feature extraction model, of the second feature extraction model, and/or of the parameter determining model.

In some embodiments, the changing, based at least in part on the one or more location deviations, one or more parameters of the first feature extraction model, of the second feature extraction model, and/or of the parameter determining model includes changing one or more parameters of the first feature extraction model, of the second feature extraction model, and/or of the parameter determining model to reduce the one or more location deviations.

In some embodiments, the non-transitory computer-readable medium, that when executed by a processor, further causes the processor to perform: determining one or more target feature depths corresponding to the depth image based at least in part on the three-dimensional model parameters. In certain examples, the receiving a ground truth includes receiving one or more reference feature depths corresponding to the depth image. In some examples, the determining a deviation includes determining one or more depth deviations between the one or more target feature depths and the one or more reference feature depths. In various examples, the changing, based at least in part on the deviation, one or more parameters of the first feature extraction model, of the second feature extraction model, and/or of the parameter determining model includes changing, based at least in part on the one or more depth deviations, one or more parameters of the first feature extraction model, of the second feature extraction model, and/or of the parameter determining model.

In some embodiments, the changing, based at least in part on the one or more depth deviations, one or more parameters of the first feature extraction model, of the second feature extraction model, and/or of the parameter determining model includes changing one or more parameters of the first feature extraction model, of the second feature extraction model, and/or of the parameter determining model to reduce the one or more depth deviations.

In some embodiments, the non-transitory computer-readable medium, that when executed by a processor, further causes the processor to perform: generating, by a distribution generating model, a target distribution of a target latent vector based at least in part on the plurality of three-dimensional model parameters. In certain examples, the receiving a ground truth includes receiving a normal distribution. In some examples, the determining a deviation includes determining a target distribution divergence of the target distribution from the normal distribution. In various examples, the changing, based at least in part on the deviation, one or more parameters of the first feature extraction model, of the second feature extraction model, and/or of the parameter determining model includes changing, based at least in part on the target distribution divergence, one or more parameters of the first feature extraction model, of the second feature extraction model, and/or of the parameter determining model.

In some embodiments, the changing, based at least in part on the target distribution divergence, one or more parameters of the first feature extraction model, of the second feature extraction model, and/or of the parameter determining model includes changing, one or more parameters of the first feature extraction model, of the second feature extraction model, and/or of the parameter determining model to reduce the target distribution divergence.

In some embodiments, the non-transitory computer-readable medium, that when executed by a processor, further causes the processor to perform: training the distribution generating model by at least: receiving one or more training parameters corresponding to a reference image of a patient having a realistic shape and/or a realistic pose; generating, by the distribution generating model, a training distribution of a training latent vector based at least in part on the one or more training parameters; determining a training distribution divergence of the training distribution from the normal distribution; and changing one or more parameters of the distribution generating model based at least in part on the training distribution divergence.

In some embodiments, the changing one or more parameters of the distribution generating model based at least in part on the training distribution divergence includes changing one or more parameters of the distribution generating model to reduce the training distribution divergence.

In some embodiments, the determining a training distribution divergence of the training distribution from the normal distribution includes determining a Kullback-Leibler divergence.

In some embodiments, the non-transitory computer-readable medium, that when executed by a processor, further causes the processor to perform: generating a three-dimensional patient representation based at least in part on the plurality of three-dimensional patient parameters; and/or providing the three-dimensional patient representation as medical guidance.

In some embodiments, the plurality of three-dimensional patient parameters includes a pose parameter and/or a shape parameter. In certain examples, the medical guidance includes guidance for medical scanner positioning, medical scanning parameters optimization; and/or medical treatment sequence planning.

In various embodiments, a computer-implemented method for providing medical guidance includes: receiving, by a first feature extraction model, a depth image; receiving, by a second feature extraction model, a two-dimensional image; generating, by the first feature extraction model, a first feature vector corresponding to the depth image; generating, by the second feature extraction model, a second feature vector corresponding to the two-dimensional image; concatenating the first feature vector and the second feature vector into a concatenated feature vector; determining, by a parameter determining model, a plurality of three-dimensional patient parameters based at least in part on the concatenated feature vector; and providing the plurality of three-dimensional patient parameters as medical guidance. In certain examples, the computer-implemented method is performed by one or more processors. In some examples, the computer-implemented method is implemented at least partly according to the method S200 of FIG. 3, and/or the method S400 of FIG. 5. In certain examples, the method is implemented at least partly by the system 10 of FIG. 1.

In some embodiments, the computer-implemented method further includes: generating a three-dimensional patient representation based at least in part on the plurality of three-dimensional patient parameters; and/or providing the three-dimensional patient representation as medical guidance.

In some embodiments, the plurality of three-dimensional patient parameters includes a pose parameter and/or a shape parameter. In certain examples, the medical guidance includes guidance for medical scanner positioning, medical scanning parameters optimization; and/or medical treatment sequence planning.

In various embodiments, a system for providing medical guidance includes: an image receiving module configured to receive, by a first feature extraction model, a depth image, and receive, by a second feature extraction model, a two-dimensional image; a feature vector generating module configured to generate, by the first feature extraction model, a first feature vector corresponding to the depth image, and generate, by the second feature extraction model, a second feature vector corresponding to the two-dimensional image; a vector concatenating module configured to concatenate the first feature vector and the second feature vector into a concatenated feature vector; a parameter determining module configured to determine, by a parameter determining model, a plurality of three-dimensional patient parameters based at least in part on the concatenated feature vector; and a guidance providing module configured to provide the plurality of three-dimensional patient parameters as medical guidance. In some examples, the system is implemented at least partly according to the system 10 of FIG. 1. In certain examples, the system is configured to perform, at least partly, the method S200 of FIG. 3, and/or the method S400 of FIG. 5.

In some embodiments, the guidance providing module is further configured to generate a three-dimensional patient representation based at least in part on the plurality of three-dimensional patient parameters and/or provide the three-dimensional patient representation as medical guidance.

In some embodiments, the plurality of three-dimensional patient parameters includes a pose parameter and/or a shape parameter. In certain examples, the medical guidance includes guidance for medical scanner positioning, medical scanning parameters optimization; and/or medical treatment sequence planning.

In various embodiments, a non-transitory computer-readable medium with instructions stored thereon, that when executed by a processor, causes the processor to perform one or more processes including: receiving, by a first feature extraction model, a depth image; receiving, by a second feature extraction model, a two-dimensional image; generating, by the first feature extraction model, a first feature vector corresponding to the depth image; generating, by the second feature extraction model, a second feature vector corresponding to the two-dimensional image; concatenating the first feature vector and the second feature vector into a concatenated feature vector; determining, by a parameter determining model, a plurality of three-dimensional patient parameters based at least in part on the concatenated feature vector; and providing the plurality of three-dimensional patient parameters as medical guidance. In some examples, the non-transitory computer-readable medium with instructions stored thereon is implemented according to the method S200 of FIG. 3, and/or the method S400 of FIG. 5. In certain examples, the non-transitory computer-readable medium with instructions stored thereon is configured to be implemented at least partly by the system 10 (e.g., a terminal) of FIG. 1.

In some embodiments, the non-transitory computer-readable medium, that when executed by a processor, further causes the processor to perform: generating a three-dimensional patient representation based at least in part on the plurality of three-dimensional patient parameters; and/or providing the three-dimensional patient representation as medical guidance.

In some embodiments, the plurality of three-dimensional patient parameters includes a pose parameter and/or a shape parameter. In certain examples, the medical guidance includes guidance for medical scanner positioning, medical scanning parameters optimization; and/or medical treatment sequence planning.

In certain embodiments, a computer-implemented method for training a patient representation model includes: receiving, by a first neural network, a depth image; receiving, by a second neural network, a two-dimensional image; generating, by the first neural network, a first feature vector corresponding to the depth image; generating, by the second neural network, a second feature vector corresponding to the two-dimensional image; concatenating the first feature vector and the second feature vector into a concatenated feature vector; determining, by a third neural network, a plurality of three-dimensional model parameters based at least in part on the concatenated feature vector; receiving a ground truth corresponding to the depth image and/or the two-dimensional image; determining a deviation between the ground truth and information associated with the plurality of three-dimensional model parameters; and changing, based at least in part on the deviation, one or more parameters of the first neural network, of the second neural network, and/or of the third neural network.

In certain examples, the receiving a ground truth includes receiving a plurality of ground truth model parameters corresponding to the depth image and the two-dimensional image; the determining a deviation includes determining a model deviation between the plurality of three-dimensional model parameters and the plurality of ground truth model parameters; and the changing, based at least in part on the deviation, one or more parameters of the first neural network, of the second neural network, and/or of the third neural network includes changing, based at least in part on the model deviation, one or more parameters of the first neural network, of the second neural network, and/or of the third neural network.

In certain examples, the changing, based at least in part on the model deviation, one or more parameters of the first neural network, of the second neural network, and/or of the third neural network includes changing one or more parameters of the first neural network, of the second neural network, and/or of the third neural network to reduce the model deviation.

In certain examples, the determining a model deviation includes determining a deviation distance based at least in part on the plurality of three-dimensional model parameters and the plurality of ground truth parameters.

In certain examples, the computer-implemented method further includes determining one or more target feature locations corresponding to the two-dimensional image based at least in part on the plurality of three-dimensional model parameters. In some examples, the receiving a ground truth includes receiving one or more reference feature locations corresponding to the two-dimensional image; the determining a deviation includes determining one or more location deviations between the one or more target feature locations and the one or more reference feature locations; and the changing, based at least in part on the deviation, one or more parameters of the first neural network, of the second neural network, and/or of the third neural network includes changing, based at least in part on the one or more location deviations, one or more parameters of the first neural network, of the second neural network, and/or of the third neural network.

In certain examples, the changing, based at least in part on the one or more location deviations, one or more parameters of the first neural network, of the second neural network, and/or of the third neural network includes changing one or more parameters of at least one of the second neural network, of the first neural network, and/or of the third neural network to reduce the one or more location deviations.

In certain examples, the determining one or more location deviations includes determining a deviation distance based at least in part on the one or more target locations and the one or more reference feature locations.

In certain examples, the computer-implemented method of claim 1 further includes determining one or more target feature depths corresponding to the depth image based at least in part on the three-dimensional model parameters. In some examples, the receiving a ground truth includes receiving one or more reference feature depths corresponding to the depth image; the determining a deviation includes determining one or more depth deviations between the one or more target feature depths and the one or more reference feature depths; and the changing, based at least in part on the deviation, one or more parameters of the first neural network, of the second neural network, and/or of the third neural network includes changing, based at least in part on the one or more depth deviations, one or more parameters of the first neural network, of the second neural network, and/or of the third neural network.

In certain examples, the changing, based at least in part on the one or more depth deviations, one or more parameters of the first neural network, of the second neural network, and/or of the third neural network includes changing one or more parameters of the first neural network, of the second neural network, and/or of the third neural network to reduce the one or more depth deviations.

In certain examples, the determining one or more depth deviations includes determining a deviation distance based at least in part on the one or more target feature depths and the one or more reference feature depths.

In certain examples, the computer-implemented method further includes generating, by a fourth neural network, a target distribution of a target latent vector based at least in part on the plurality of three-dimensional model parameters. In some examples, the receiving a ground truth includes receiving a normal distribution; the determining a deviation includes determining a target distribution divergence of the target distribution from the normal distribution; and the changing, based at least in part on the deviation, one or more parameters of the first neural network, of the second neural network, and/or of the third neural network includes changing, based at least in part on the target distribution divergence, one or more parameters of the first neural network, of the second neural network, and/or of the third neural network.

In certain examples, the changing, based at least in part on the target distribution divergence, one or more parameters of the first neural network, of the second neural network, and/or of the third neural network includes changing, one or more parameters of the first neural network, of the second neural network, and/or of the third neural network to reduce the target distribution divergence.

In certain examples, the computer-implemented method further includes training the fourth neural network by at least: receiving one or more training parameters corresponding to a reference image of a patient having a realistic shape and a realistic pose; generating, by the fourth neural network, a training distribution of a training latent vector based at least in part on the one or more training parameters; determining a training distribution divergence of the training distribution from the normal distribution; and changing one or more parameters of the fourth neural network based at least in part on the training distribution divergence.

In certain examples, the changing one or more parameters of the fourth neural network based at least in part on the training distribution divergence includes changing one or more parameters of the fourth neural network to reduce the training distribution divergence.

In certain examples, the determining a training distribution divergence of the training distribution from the normal distribution includes determining a Kullback-Leibler divergence.

In certain examples, the plurality of three-dimensional model parameters includes a pose parameter and/or a shape parameter.

In certain embodiments, a computer-implemented method for generating a three-dimensional patient representation includes: receiving, by a first neural network, a depth image; receiving, by a second neural network, a two-dimensional image; generating, by the first neural network, a first feature vector corresponding to the depth image; generating, by the second neural network, a second feature vector corresponding to the two-dimensional image; concatenating the first feature vector and the second feature vector into a concatenated feature vector; determining, by a third neural network, a plurality of three-dimensional model parameters based at least in part on the concatenated feature vector; and generating a three-dimensional patient representation based at least in part on the plurality of three-dimensional model parameters; and providing the three-dimensional patient representation for use in medical environments. In some examples, the plurality of three-dimensional model parameters includes a pose parameter and/or a shape parameter.

In certain examples, the computer-implemented method further includes acquiring the depth image and/or the two-dimensional image using a RGB sensor, a RGBD sensor, a laser sensor, a FIR sensor, a NIR sensor, and/or a lidar sensor.

In certain examples, the three-dimensional patient representation includes an image, a kinematic model, a skeleton model, a surface model, a mesh model, a fitted model, and/or a point cloud.

In certain embodiments, a system for generating a three-dimensional patient representation includes an image receiving module configured to: receive, by a first neural network, a depth image, and receive, by a second neural network, a two-dimensional image; a feature vector generating module configured to: generate, by the first neural network, a first feature vector corresponding to the depth image, and generate, by the second neural network, a second feature vector corresponding to the two-dimensional image; a vector concatenating module configured to concatenate the first feature vector and the second feature vector into a concatenated feature vector; a model parameter determining module configured to determine, by a third neural network, a plurality of three-dimensional model parameters based at least in part on the concatenated feature vector; and a patient representation generating module configured to generate a three-dimensional patient representation based at least in part on the plurality of three-dimensional model parameters; and a patient representation providing module configured to provide the three-dimensional patient representation for use in medical environments. In some examples, the plurality of three-dimensional model parameters includes a pose parameter and a shape parameter.

For example, some or all components of various embodiments of the present invention each are, individually and/or in combination with at least another component, implemented using one or more software components, one or more hardware components, and/or one or more combinations of software and hardware components. In another example, some or all components of various embodiments of the present invention each are, individually and/or in combination with at least another component, implemented in one or more circuits, such as one or more analog circuits and/or one or more digital circuits. In yet another example, while the embodiments described above refer to particular features, the scope of the present invention also includes embodiments having different combinations of features and embodiments that do not include all of the described features. In yet another example, various embodiments and/or examples of the present invention can be combined.

Additionally, the methods and systems described herein may be implemented on many different types of processing devices by program code including program instructions that are executable by the device processing subsystem. The software program instructions may include source code, object code, machine code, or any other stored data that is operable to cause a processing system to perform the methods and operations described herein. Other implementations may also be used, however, such as firmware or even appropriately designed hardware configured to perform the methods and systems described herein.

The systems' and methods' data (e.g., associations, mappings, data input, data output, intermediate data results, final data results, etc.) may be stored and implemented in one or more different types of computer-implemented data stores, such as different types of storage devices and programming constructs (e.g., RAM, ROM, EEPROM, Flash memory, flat files, databases, programming data structures, programming variables, IF-THEN (or similar type) statement constructs, application programming interface, etc.). It is noted that data structures describe formats for use in organizing and storing data in databases, programs, memory, or other computer-readable media for use by a computer program.

The systems and methods may be provided on many different types of computer-readable media including computer storage mechanisms (e.g., CD-ROM, diskette, RAM, flash memory, computer's hard drive, DVD, etc.) that contain instructions (e.g., software) for use in execution by a processor to perform the methods' operations and implement the systems described herein. The computer components, software modules, functions, data stores and data structures described herein may be connected directly or indirectly to each other in order to allow the flow of data needed for their operations. It is also noted that a module or processor includes a unit of code that performs a software operation and can be implemented for example as a subroutine unit of code, or as a software function unit of code, or as an object (as in an object-oriented paradigm), or as an applet, or in a computer script language, or as another type of computer code. The software components and/or functionality may be located on a single computer or distributed across multiple computers depending upon the situation at hand.

The computing system can include client devices and servers. A client device and server are generally remote from each other and typically interact through a communication network. The relationship of client device and server arises by virtue of computer programs running on the respective computers and having a client device-server relationship to each other.

This specification contains many specifics for particular embodiments. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations, one or more features from a combination can in some cases be removed from the combination, and a combination may, for example, be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Although specific embodiments of the present invention have been described, it will be understood by those of skill in the art that there are other embodiments that are equivalent to the described embodiments. Accordingly, it is to be understood that the invention is not to be limited by the specific illustrated embodiments.

What is claimed is:

1. A computer-implemented method for providing medical guidance, the method comprising:
   receiving a patient representation model including one or more feature extraction models and a parameter determining model;
   receiving, by the one or more feature extraction models, one or more patient images, the one or more patient images comprising a patient depth image and a patient two-dimensional image;
   generating, by a first feature extraction model of the one or more feature extraction models, a first patient feature vector corresponding to the patient depth image;
   generating, by a second feature extraction model of the one or more feature extraction models, a second patient feature vector corresponding to the patient two-dimensional image;
   concatenating the first patient feature vector and the second patient feature vector into a concatenated patient feature vector;
   determining, by the parameter determining model, a plurality of three-dimensional patient parameters based at least in part on the concatenated patient feature vector; and
   providing the plurality of three-dimensional patient parameters as medical guidance;
   wherein the patient representation model is updated by at least:
     receiving a depth image and a two-dimensional image;
     generating, by the first feature extraction model, a first feature vector corresponding to the depth image;
     generating, by the second feature extraction model, a second feature vector corresponding to the two-dimensional image;
     concatenating the first feature vector and the second feature vector into a concatenated feature vector;
     determining, by the parameter determining model, a plurality of three-dimensional model parameters based at least in part on the concatenated feature vector;
     receiving a ground truth corresponding to the depth image and the two-dimensional image;
     determining a deviation between the ground truth and information associated with the plurality of three-dimensional model parameters; and
     changing one or more parameters of the patient representation model based at least in part on the deviation, wherein the changing one or more parameters of the patient representation model comprises changing, based at least in part on the deviation, one or more parameters of at least one selected from a group consisting of the first feature extraction model, the second feature extraction model, and the parameter determining model.

2. The computer-implemented method of claim 1, wherein:
   the receiving a ground truth includes receiving a plurality of ground truth model parameters corresponding to the depth image; and
   the determining a deviation includes determining a deviation distance between the plurality of three-dimensional model parameters and the plurality of ground truth model parameters.

3. The computer-implemented method of claim 2, wherein the changing one or more parameters of the patient representation model comprising changing the one or more parameters of the patient representation model to reduce the deviation distance.

4. The computer-implemented method of claim 1, wherein:
   the receiving a ground truth includes receiving one or more reference feature locations corresponding to the two-dimensional image;
   the determining a deviation includes:
     determining one or more target feature locations corresponding to the two-dimensional image based at least in part on the plurality of three-dimensional model parameters;
     determining one or more location deviations between the one or more target feature locations and the one or more reference feature locations; and
   the changing one or more parameters of patient representation model comprises changing the one or more parameters of patient representation model based at least in part on the one or more location deviations.

5. The computer-implemented method of claim 4, wherein the changing one or more parameters of patient representation model comprises changing the one or more parameters of patient representation model based at least in part on the one or more location deviations to reduce the one or more location deviations.

6. The computer-implemented method of claim 1, wherein:
   the receiving a ground truth includes receiving one or more reference feature depths corresponding to the depth image;
   the determining a deviation includes:
   determining one or more target feature depths corresponding to the depth image based at least in part on the three-dimensional model parameters; and
   determining one or more depth deviations between the one or more target feature depths and the one or more reference feature depths; and
   the changing one or more parameters of patient representation model comprises changing the one or more parameters of patient representation model based at least in part on based at least in part on the one or more depth deviations.

7. The computer-implemented method of claim 6, wherein the changing one or more parameters of patient representation model comprises changing the one or more parameters of patient representation model based at least in part on the one or more depth deviations to reduce the one or more depth deviations.

8. The computer-implemented method of claim 1, wherein:
   the receiving a ground truth includes receiving a normal distribution;

the determining a deviation includes:
    generating, by a distribution generating model, a target distribution of a target latent vector based at least in part on the plurality of three-dimensional model parameters; and
    determining a target distribution divergence of the target distribution from the normal distribution; and
the changing one or more parameters of patient representation model comprises changing the one or more parameters of patient representation model based at least in part on the target distribution divergence.

9. The computer-implemented method of claim 8, wherein the changing one or more parameters of patient representation model comprises changing the one or more parameters of patient representation model based at least in part on the target distribution divergence to reduce the target distribution divergence.

10. The computer-implemented method of claim 8, wherein the distribution generating model is trained by at least:
    receiving one or more training parameters corresponding to a reference image of a patient having a realistic shape and a realistic pose;
    generating, by the distribution generating model, a training distribution of a training latent vector based at least in part on the one or more training parameters;
    determining a training distribution divergence of the training distribution from the normal distribution; and
    changing one or more parameters of the distribution generating model based at least in part on the training distribution divergence.

11. The computer-implemented method of claim 10, wherein the changing one or more parameters of the distribution generating model based at least in part on the training distribution divergence includes changing one or more parameters of the distribution generating model to reduce the training distribution divergence.

12. The computer-implemented method of claim 10, wherein the determining a training distribution divergence of the training distribution from the normal distribution includes determining a Kullback-Leibler divergence.

13. The computer-implemented method of claim 1, further comprising:
    generating a three-dimensional patient representation based at least in part on the plurality of three-dimensional patient parameters; and
    providing the three-dimensional patient representation as medical guidance.

14. The computer-implemented method of claim 13, wherein the plurality of three-dimensional patient parameters includes a pose parameter and a shape parameter;
    wherein the medical guidance includes guidance for at least one selected from a group consisting of medical scanner positioning, medical scanning parameters optimization, and medical treatment sequence planning.

15. A system for providing medical guidance, the system comprising:
    one or more memories comprising computer executable instructions stored thereon;
    one or more processors coupled to the one or more memories and configured to execute the computer executable instructions to perform the operations comprising:
        receiving a patient representation model including one or more feature extraction models and a parameter determining model;
        receiving, by the one or more feature extraction models, one or more patient images, the one or more patient images comprising a patient depth image and a patient two-dimensional image;
        generating, by a first feature extraction model of the one or more feature extraction models, a first patient feature vector corresponding to the patient depth image;
        generating, by a second feature extraction model of the one or more feature extraction models, a second patient feature vector corresponding to the patient two-dimensional image;
        concatenating the first patient feature vector and the second patient feature vector into a concatenated patient feature vector;
        determining, by the parameter determining model, a plurality of three-dimensional patient parameters based at least in part on the concatenated patient feature vector; and
        providing the plurality of three-dimensional patient parameters as medical guidance;
    wherein the patient representation model is updated by at least:
        receiving a depth image and a two-dimensional image;
        generating, by the first feature extraction model, a first feature vector corresponding to the depth image;
        generating, by the second feature extraction model, a second feature vector corresponding to the two-dimensional image;
        concatenating the first feature vector and the second feature vector into a concatenated feature vector;
        determining, by the parameter determining model, a plurality of three-dimensional model parameters based at least in part on the concatenated feature vector;
        receiving a ground truth corresponding to the depth image and the two-dimensional image;
        determining a deviation between the ground truth and information associated with the plurality of three-dimensional model parameters; and
        changing one or more parameters of the patient representation model based at least in part on the deviation, wherein the changing one or more parameters of the patient representation model comprises changing, based at least in part on the deviation, one or more parameters of at least one selected from a group consisting of the first feature extraction model, the second feature extraction model, and the parameter determining model.

16. The system of claim 15, wherein:
the receiving a ground truth includes receiving a normal distribution;
the determining a deviation includes:
    generating, by a distribution generating model, a target distribution of a target latent vector based at least in part on the plurality of three-dimensional model parameters; and
    determining a target distribution divergence of the target distribution from the normal distribution; and
the changing one or more parameters of patient representation model comprises changing the one or more parameters of patient representation model based at least in part on the target distribution divergence.

17. The system of claim 16, wherein the changing one or more parameters of patient representation model comprises changing the one or more parameters of patient representation model based at least in part on the target distribution divergence to reduce the target distribution divergence.

18. The system of claim 16, wherein the distribution generating model is trained by at least:
- receiving one or more training parameters corresponding to a reference image of a patient having a realistic shape and a realistic pose;
- generating, by the distribution generating model, a training distribution of a training latent vector based at least in part on the one or more training parameters;
- determining a training distribution divergence of the training distribution from the normal distribution; and
- changing one or more parameters of the distribution generating model based at least in part on the training distribution divergence.

19. The system of claim 18, wherein the changing one or more parameters of the distribution generating model based at least in part on the training distribution divergence includes changing one or more parameters of the distribution generating model to reduce the training distribution divergence.

20. The system of claim 15, wherein the operations further comprise:
- generating a three-dimensional patient representation based at least in part on the plurality of three-dimensional patient parameters; and
- providing the three-dimensional patient representation as medical guidance.

* * * * *